United States Patent
Boldingh et al.

(10) Patent No.: US 11,084,766 B1
(45) Date of Patent: *Aug. 10, 2021

(54) TOLUENE DISPROPORTIONATION USING AN ENHANCED UZM-39 ALUMINOSILICATE ZEOLITE

(71) Applicant: UOP LLC, Des Plaines, IL (US)

(72) Inventors: Edwin P. Boldingh, Arlington Heights, IL (US); Christopher P. Nicholas, Evanston, IL (US); Martha Leigh Abrams, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/793,527

(22) Filed: Feb. 18, 2020

(51) Int. Cl.
| | |
|---|---|
| C07C 6/12 | (2006.01) |
| B01J 37/08 | (2006.01) |
| B01J 29/70 | (2006.01) |
| B01J 21/08 | (2006.01) |
| B01J 21/18 | (2006.01) |
| B01J 37/10 | (2006.01) |
| B01J 37/02 | (2006.01) |

(52) U.S. Cl.
CPC ............ *C07C 6/126* (2013.01); *B01J 21/08* (2013.01); *B01J 21/18* (2013.01); *B01J 29/70* (2013.01); *B01J 37/0215* (2013.01); *B01J 37/10* (2013.01); *B01J 2229/186* (2013.01); *B01J 2229/36* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 4,016,219 A | 4/1977 | Kaeding | |
| 4,097,543 A * | 6/1978 | Haag | B01J 29/40 585/471 |
| 4,629,717 A | 12/1986 | Chao | |
| 6,114,592 A | 9/2000 | Gajda et al. | |
| 6,359,185 B1 * | 3/2002 | Boldingh | B01J 29/40 502/214 |
| 6,429,347 B1 | 8/2002 | Boldingh | |
| 6,613,302 B1 | 9/2003 | Moscoso et al. | |
| 6,756,030 B1 | 6/2004 | Rohde et al. | |
| 6,776,975 B2 | 8/2004 | Wilson et al. | |
| 7,575,737 B1 | 8/2009 | Miller et al. | |

(Continued)

FOREIGN PATENT DOCUMENTS

| | | |
|---|---|---|
| CN | 104870368 A | 8/2015 |
| WO | 9616004 | 5/1996 |
| WO | 2014099325 A1 | 6/2014 |

OTHER PUBLICATIONS

International Search Report from corresponding PCT application No. PCT/US2021/017633, dated May 27, 2021.

(Continued)

*Primary Examiner* — Philip Y Louie

(57) ABSTRACT

Toluene disproportionation processes utilizing treated UZM-39 zeolites are described. The processes produce effluent streams comprising para-xylene and benzene. The molar ratio of benzene to xylene (Bz/X) in the effluent stream can be in a range of about 1.00 to about 1.14, the molar ratio of para-xylene to xylene (pX/X) in the effluent stream can be in a range of about 0.80 to about 1.0, and the conversion of toluene can be about 20% to about 40%.

18 Claims, 5 Drawing Sheets

(56) References Cited

U.S. PATENT DOCUMENTS

| | | |
|---|---|---|
| 7,713,513 B2 | 5/2010 | Jan et al. |
| 8,642,823 B2 | 2/2014 | Nicholas et al. |
| 8,846,998 B2 | 9/2014 | Nicholas et al. |
| 8,927,798 B2 | 1/2015 | Nicholas et al. |
| 8,940,952 B2 | 1/2015 | Nicholas et al. |
| 8,946,497 B1 | 2/2015 | Nicholas et al. |
| 8,993,921 B2 | 3/2015 | Jan et al. |
| 2010/0152023 A1 | 6/2010 | Miller et al. |
| 2014/0163286 A1* | 6/2014 | Nicholas ............... C07C 6/126 585/475 |

OTHER PUBLICATIONS

Written Opinion from from corresponding PCT application No. PCT/US2021/017633, dated Apr. 16, 2021.

* cited by examiner

TOLUENE DISPROPORTIONATION USING AN ENHANCED UZM-39 ALUMINOSILICATE ZEOLITE

BACKGROUND

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

One particular zeolite, designated TNU-9, was first disclosed by Hong et al. in 2004 (J. Am. Chem. Soc. 2004, 126, 5817-26) and then in a Korean Patent granted in 2005, KR 480229. This report and patent was followed by a full report of the synthesis in 2007 (J. Am. Chem. Soc. 2007, 129, 10870-85). These papers describe the synthesis of TNU-9 from the flexible dicationic structure directing agent, 1,4-bis(N-methylpyrrolidinium)butane dibromide in the presence of sodium. After the structure of TNU-9 was solved (Nature, 2006, 444, 79-81), the International Zeolite Association Structure Commission gave the code of TUN to this zeolite structure type, see Atlas of Zeolite Framework Types, which is maintained by the International Zeolite Association Structure Commission at http://www.iza-structure.org/databases/. The TUN structure type was found to contain 3 mutually orthogonal sets of channels in which each channel is defined by a 10-membered ring of tetrahedrally coordinated atoms. In addition, 2 different sizes of 10-membered ring channels exist in the structure.

Another particular zeolite, IM-5 was first disclosed by Benazzi, et al. in 1996 (FR96/12873; WO98/17581) who describe the synthesis of IM-5 from the flexible dicationic structure directing agent, 1,5-bis(N-methylpyrrolidinium) pentane dibromide or 1,6-bis(N-methylpyrrolidinium) hexane dibromide in the presence of sodium. After the structure of IM-5 was solved by Baerlocher et al. (Science, 2007, 315, 113-6), the International Zeolite Structure Commission gave the code of IMF to this zeolite structure type, see Atlas of Zeolite Framework Types. The IMF structure type was also found to contain three mutually orthogonal sets of channels in which each channel is defined by a 10-membered ring of tetrahedrally coordinated atoms, however, connectivity in the third dimension is interrupted every 2.5 nm, therefore diffusion is somewhat limited. In addition, multiple different sizes of 10-membered ring channels exist in the structure.

Applicants previously developed a new family of materials designated UZM-39. The topology of the materials is similar to that observed for TNU-9 and IM-5. The materials may be used in various hydrocarbon conversion processes, as described in U.S. Pat. Nos. 8,642,823, 8,940,952, 8,946,497, and 8,846,998.

The xylene isomers are produced in large volumes from petroleum as feedstocks for a variety of important industrial chemicals. The most important of the xylene isomers is para-xylene, the principal feedstock for polyester which continues to enjoy a high growth rate from large base demand Ortho-xylene is used to produce phthalic anhydride, which has high-volume, but mature markets. Meta-xylene is used in lesser but growing volumes for such products as plasticizers, azo dyes, and wood preservers.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand. Therefore, conversion of other hydrocarbons is necessary to increase production of xylenes and benzene. Often toluene is selectively disproportionated to yield benzene and $C_8$ aromatics from which the individual xylene isomers are recovered.

Para-selective toluene disproportionation is a process that was commercialized in the 1980's with the aim of converting toluene to benzene and xylenes with high para-xylene to total xylenes molar ratio (pX/X molar ratio) of typically greater than 0.85. This technology is particularly desired when there is a demand for polyesters and other chemicals derived from para-xylene, but limited demand for other xylenes. High pX/X was initially achieved by "selectivation" of the catalyst with carbon and/or coke to narrow the MFI pore size and to cover acid sites on the exterior surface of the MFI crystals. Later, it was learned that depositing silica on the catalyst achieved similar results.

U.S. Pat. No. 4,016,219 B1 (Kaeding) discloses a process for toluene disproportionation using a catalyst comprising a zeolite which has been modified by the addition of phosphorus in an amount of at least 0.5 mass-%. The crystals of the zeolite are contacted with a phosphorus compound to effect reaction of the zeolite and phosphorus compound. The modified zeolite then may be incorporated into indicated matrix materials.

U.S. Pat. No. 4,097,543 B1 (Haag et al.) teaches toluene disproportionation for the selective production of para-xylene using a zeolite which has undergone controlled pre-coking. The zeolite may be ion-exchanged with a variety of elements from Group IB to VIII, and composited with a variety of clays and other porous matrix materials.

U.S. Pat. No. 6,114,592 B1 (Gajda et al.), teaches an improved process combination for the selective disproportionation of toluene. The combination comprises selective hydrogenation of a toluene feedstock followed by contacting with a zeolitic catalyst which has been oil-dropped in an aluminum phosphate binder to achieve a high yield of para-xylene.

U.S. Pat. No. 6,429,347 B1 (Boldingh) teaches toluene disproportionation for the selective production of para-xylene using a catalyst comprising MFI zeolite bound with alumina phosphate after selectively pre-coking the catalyst by contacting the catalyst with a coke-forming feed at pre-coking conditions.

In these processes, the zeolite of choice was ZSM-5 which has an MFI framework. Using these catalysts, the molar ratio of para-xylene to xylene (pX/X) can be increased from the equilibrium level of about 0.24 to 0.90 or more by deposition of sufficient amounts of coke or silica. Although this increases the pX/X molar ratio, it is always accompanied by an increase in the molar ratio of benzene to xylene (Bz/X) to significantly greater than the theoretical value of 1. The higher the pX/X molar ratio, the higher the Bz/X molar ratio.

Although not wishing to be bound by theory, it appears the increase in the Bz/X molar ratio is caused by a loss in total xylene yield. In general, as the para-xylene yield is increased beyond a certain level, the total xylene yield typically decreases. This is considered inevitable, and much research has been aimed at optimizing the use of coke or silica to minimize Bz/X molar ratio. Using the best silica deposition technology to increase pX/X molar ratio to 0.90 or more, it is quite common to see Bz/X molar ratio values up to 1.4 at disproportionation conditions of 30% toluene conversion, $H_2/HC=2$, WHSV=4, at a pressure of 400 psig.

Therefore, there is a need for an improved toluene disproportionation process in which the pX/X molar ratio is high (e.g., 0.70 or more) and the Bz/X molar ratio is less than 1.2.

DETAILED DESCRIPTION

Figure 1:
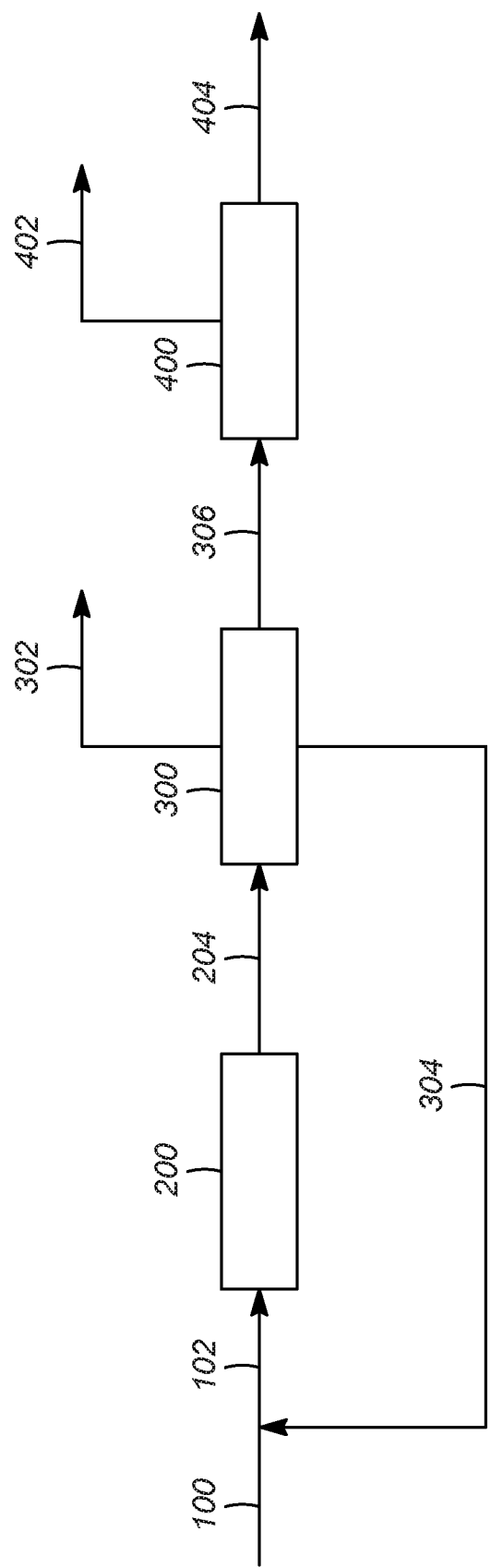
FIG. 1 is an illustration of one embodiment of a toluene disproportionation process.

One aspect of the invention is a toluene disproportionation process. In one embodiment, the process comprises contacting a feed comprising toluene with a microporous crystalline zeolite at disproportionation conditions to produce an effluent stream comprising para-xylene and benzene, wherein a molar ratio of benzene to xylene (Bz/X) in the effluent stream is in a range of about 1.00 to about 1.14, wherein a molar ratio of para-xylene to xylene (pX/X) in the effluent stream is in a range of about 0.80 to about 1.0, and wherein a conversion of toluene is about 20% to about 40%.

The present invention relates to the catalytic use of an aluminosilicate zeolite designated UZM-39. UZM-39 is a zeolite whose topological structure is related to TUN as described in Atlas of Zeolite Framework Types, which is maintained by the International Zeolite Association Structure Commission at http://www.iza-structure.org/databases/, the member of which has been designated TNU-9. However, UZM-39 is different from TNU-9 in a number of its characteristics including its x-ray diffraction pattern (XRD). UZM-39 is also related to IMF as described in the Atlas of Zeolite Framework Types, the member of which has been designated IM-5. UZM-39 is different from TNU-9 and IM-5 in a number of its characteristics including its x-ray diffraction pattern as shown in in U.S. Pat. Nos. 8,642,823, 8,940,952, 8,946,497, and 8,846,998, each of which is incorporated herein by reference in its entirety, describing the preparation and use of UZM-39. It has been surprisingly found that UZM-39 which has undergone an enhancement step until the pX/X molar ratio is greater than 0.75 during disproportionation conditions had a unique combination of high pX/X molar ratio and high total xylene selectivity without production of excess benzene.

UZM-39 has an empirical composition in the as synthesized and anhydrous basis expressed by an empirical formula of:

$$Na_nM_m^{k+}T_tAl_{1-x}E_xSi_yO_z$$

where "n" is the mole ratio of Na to (Al+E) and has a value from approximately 0.05 to 0.5, M represents a metal or metals selected from the group consisting of zinc, Group 1 (IUPAC 1), Group 2 (IUPAC 2), Group 3 (IUPAC 3), the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having between 3 and 6 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of 0 to (Al+E) and has a value determined by the equation:

$$z=(n+k \cdot m+3+4 \cdot y)/2$$

where M is only one metal, then the weighted average valence is the valence of that one metal, i.e. +1 or +2. However, when more than one M metal is present, the total amount of:

$$M_m^{k+}=M_{m1}^{(k1)+}+M_{m2}^{(k2)+}+M_{m3}^{(k3)+}+M_{m4}^{(k4)+}+ \ldots$$

and the weighted average valence "k" is given by the equation:

$$k = \frac{m1 \cdot k1 + m2 \cdot k2 + m3 \cdot k3 \ldots}{m1 + m2 + m3 \ldots}$$

UZM-39 may be synthesized by a hydrothermal crystallization of a reaction mixture prepared by combining reactive sources of sodium, organic structure directing agent or agents T, aluminum, silicon, seeds of a layered material L, and optionally E, M, or both. The sources of aluminum include but are not limited to aluminum alkoxides, precipitated aluminas, aluminum metal, aluminum hydroxide, sodium aluminate, aluminum salts and alumina sols. Specific examples of aluminum alkoxides include, but are not limited to aluminum sec-butoxide and aluminum ortho isopropoxide. Sources of silica include but are not limited to tetraethylorthosilicate, colloidal silica, precipitated silica and alkali silicates. Sources of sodium include but are not limited to sodium hydroxide, sodium bromide, sodium aluminate, and sodium silicate.

T is the organic structure directing agent or agents derived from reactants R and Q where R is an A,Ω-dihalogen substituted alkane having between 3 and 6 carbon atoms and Q comprises at least one neutral monoamine having 6 or fewer carbon atoms. R may be an A,Ω-dihalogen substituted alkane having between 3 and 6 carbon atoms selected from the group consisting of 1,3-dichloropropane, 1,4-dichlorobutane, 1,5-dichloropentane, 1,6-dichlorohexane, 1,3-dibromopropane, 1,4-dibromobutane, 1,5-dibromopentane, 1,6-dibromohexane, 1,3-diiodopropane, 1,4-diiodobutane, 1,5-diiodopentane, 1,6-diiodohexane and combinations thereof. Q comprises at least one neutral monoamine having 6 or fewer carbon atoms such as 1-ethylpyrrolidine, 1-methylpyrrolidine, 1-ethylazetidine, 1-methylazetidine, triethylamine, diethylmethylamine, dimethylethylamine, trimethylamine, dimethylbutylamine, dimethylpropylamine, dimethylisopropylamine, methylethylpropylamine, methylethylisopropylamine, dipropylamine, diisopropylamine, cyclopentylamine, methylcyclopentylamine, hexamethyleneimine Q may comprise combinations of multiple neutral monoamines having 6 or fewer carbon atoms.

L comprises at least one seed of a layered zeolite. Suitable seed zeolites are layered materials that are microporous zeolites with crystal thickness in at least one dimension of less than about 30 to about 50 nm. The microporous materials have pore diameters of less than about 2 nm. The seed layered zeolite is of a different zeotype than the UZM-39 coherently grown composite being synthesized. Examples of suitable layered materials include but are not limited to UZM-4M (U.S. Pat. No. 6,776,975), UZM-5 (U.S. Pat. No. 6,613,302), UZM-8 (U.S. Pat. No. 6,756,030), UZM-8HS (U.S. Pat. No. 7,713,513), UZM-26 (US-2010-0152023-A1), UZM-27 (U.S. Pat. No. 7,575,737), BPH, FAU/EMT materials, *BEA or zeolite Beta, members of the MWW family such as MCM-22P and MCM-22, MCM-36, MCM-49, MCM-56, ITQ-1, ITQ-2, ITQ-30, ERB-1, EMM-10P and EMM-10, SSZ-25, and SSZ-70 as well as smaller microporous materials such as PREFER (pre ferrierite), NU-6 and the like.

M represents at least one exchangeable cation of a metal or metals from Group 1 (IUPAC 1), Group 2 (IUPAC 2), Group 3 (IUPAC 3) or the lanthanide series of the periodic table and or zinc. Specific examples of M include but are not limited to lithium, potassium, rubidium, cesium, magnesium, calcium, strontium, barium, zinc, yttrium, lanthanum, gadolinium, and mixtures thereof. Reactive sources of M include, but are not limited to, the group consisting of halide, nitrate, sulfate, hydroxide, or acetate salts. E is an element selected from the group consisting of gallium, iron, boron and combinations thereof, and suitable reactive sources include, but are not limited to, boric acid, gallium oxyhydroxide, gallium nitrate, gallium sulfate, ferric nitrate, ferric sulfate, ferric chloride and mixtures thereof.

The reaction mixture containing reactive sources of the desired components can be described in terms of molar ratios of the oxides by the formula:

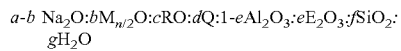

$a\text{-}b\ Na_2O{:}bM_{n/2}O{:}cRO{:}dQ{:}1\text{-}eAl_2O_3{:}eE_2O_3{:}fSiO_2{:}gH_2O$ where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. Additionally in the reaction mixture is from about 1 to about 10 wt.-% of seed zeolite L based on the amount of $SiO_2$ in the reaction, e.g., if there is 100 g of $SiO_2$ in the reaction mixture, from about 1 to about 10 g of seed zeolite L would be added. The examples demonstrate a number of specific orders of addition for the reaction mixture which lead to UZM-39. However, as there are at least 6 starting materials, many orders of addition are possible. For example, the seed crystals L can be added as the last ingredient to the reaction mixture, or to the reactive Si source, or at other suitable points. Also, if alkoxides are used, it is preferred to include a distillation or evaporative step to remove the alcohol hydrolysis products. While the organic structure directing agents R and Q can be added separately or together to the reaction mixture at a number of points in the process, it is preferred to mix R and Q together at room temperature and add the combined mixture to a cooled mixture of reactive Si, Al and Na sources maintained at 0-10° C. Alternatively, the mixture of R and Q, after mixing at room temperature, could be cooled and the reactive sources of Si, Al, and Na added to the organic structure directing agent mixture while maintaining a temperature of 0-10° C. In an alternative embodiment, the reagents R and Q could be added, separately or together, to the reaction mixture at room temperature.

The reaction mixture is then reacted at a temperature of about 150° C. to about 200° C., about 155° C. to about 190° C., or about 160° C. to about 180° C., for a period of about 1 day to about 3 weeks and preferably for a time of about 3 days to about 12 days in a stirred, sealed reaction vessel under autogenous pressure. After crystallization is complete, the solid product is isolated from the heterogeneous mixture by means such as filtration or centrifugation, and then washed with deionized water and dried in air at ambient temperature up to about 100° C.

The as-synthesized coherently grown composite of TUN and IMF zeotypes, UZM-39, is characterized by the x-ray diffraction pattern, having at least the d-spacings and relative intensities set forth in Tables A1-A3 below. Diffraction patterns herein were obtained using a typical laboratory powder diffractometer, utilizing the $K_\alpha$ line of copper; Cu K alpha. From the position of the diffraction peaks represented by the angle 2 theta (2θ), the characteristic interplanar distances $d_{hkl}$ of the sample can be calculated using the Bragg equation.

The intensity is calculated on the basis of a relative intensity scale attributing a value of 100 to the line representing the strongest peak on the X-ray diffraction pattern, and then: very weak (vw) means less than 5; weak (w) means less than 15; medium (m) means in the range 15 to 50; strong (s) means in the range 50 to 80; very strong (vs) means more than 80. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular coherently grown composite structures or for samples with crystals which are small enough to cause significant broadening of the X-rays. This can also be the case when the equipment or operating conditions used to produce the diffraction pattern differ significantly from those used in the present case. As will be understood by those skilled in the art, the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art.

The X-ray diffraction pattern for UZM-39 contains many peaks. Those peaks characteristic of UZM-39 are shown in Tables A1-A3 for various coherently grown composite structures. Additional peaks, particularly those of very weak intensity, may also be present. All peaks of medium or higher intensity present in the UZM-39 family of coherently grown composite structures are represented in at least Table A3.

Table A1 contains selected d-spacings and relative intensities of the UZM-39 X-ray diffraction pattern. The relative intensities are shown as a range covering UZM-39 materials with varying relative amounts of TUN and IMF zeotypes.

TABLE A1

| 2θ | d (Å) | I/Io % |
|---|---|---|
| 7.17-7.21 | 12.25-12.31 | vw-m |
| 7.5-8.1* | 11.78-10.91 | w-m |
| 8.88 | 9.95 | m |
| 9.17 | 9.63 | w-m |
| 12.47-12.62 | 7.09-7.00 | w-m |
| 17.7 | 5.01 | vw-m |
| 22.8-23.2 | 3.90-3.83 | vs |
| 23.39-23.49 | 3.80-3.78 | m-s |
| 25.01-25.31 | 3.56-3.52 | m |
| 28.74-29.25 | 3.10-3.05 | w-m |
| 45.08-45.29 | 2.01-2.00 | w |

*composite peak consisting of multiple overlapping reflections

The zeolite may be further characterized by the x-ray diffraction pattern having at least the d-spacings and intensities set forth in Table A2 where the d-spacings and intensities are provided at different relative concentrations of the components of the coherently grown composite structure.

TABLE A2

| I high TUN, low IMF | | | II med TUN, med IMF | | | III low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.21 | 12.25 | w-m | 7.17 | 12.31 | w-m | 7.21 | 12.25 | vw |
| 7.5-8.1* | 11.78-10.91 | w-m | 7.5-8.1* | 11.78-10.91 | w-m | 7.5-8.1* | 11.78-10.91 | w-m |
| 8.88 | 9.95 | m | 8.88 | 9.95 | s | 8.88 | 9.95 | m |
| 9.17 | 9.63 | m | 9.16 | 9.65 | m | 9.17** | 9.63 | w-m |
| 9.34** | 9.46 | vw-w | 9.30 | 9.50 | m | 9.33 | 9.47 | m |
| 12.62 | 7.00 | w | 12.50 | 7.08 | w-m | 12.47 | 7.09 | w-m |
| 17.70 | 5.01 | vw-w | 17.72 | 5.00 | w-m | 17.70 | 5.01 | vw-w |
| 19.20 | 4.62 | w-m | 22.8-23.2* | 3.90-3.83 | vs | 18.71 | 4.74 | w-m |
| 22.89 | 3.88 | vs | 23.43 | 3.79 | s | 22.55 | 3.94 | m |
| 23.49 | 3.78 | m | 25.12 | 3.54 | m | 23.03 | 3.86 | vs |
| 25.31 | 3.52 | m | 28.74-29.25* | 3.10-3.05 | w-m | 23.39 | 3.80 | s |
| 29.10 | 3.07 | w | 45.29 | 2.00 | w | 25.01 | 3.56 | m |
| 45.08 | 2.01 | w | | | | 28.76 | 3.10 | w-m |
| | | | | | | 45.08 | 2.01 | w |

*composite peak consisting of multiple overlapping reflections
**typically a shoulder The zeolite may be yet further characterized by the x-ray diffraction pattern having at least the d-spacings and intensities set forth in Table A3 where the d-spacings and intensities are provided at different relative concentrations of the components of the coherently grown composite structure.

TABLE A3

| I high TUN, low IMF | | | II med TUN, med IMF | | | III low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.21 | 12.25 | w-m | 7.17 | 12.31 | w-m | 7.21 | 12.22 | vw |
| 7.5-8.1* | 11.78-10.91 | w-m | 7.5-8.1* | 11.78-10.91 | w-m | 7.5-8.1* | 11.78-10.91 | w-m |
| 8.88 | 9.95 | m | 8.88 | 9.95 | m-s | 8.88 | 9.95 | m |
| 9.17 | 9.63 | m | 9.16 | 9.65 | m | 9.17** | 9.63 | w-m |
| 9.34** | 9.46 | vw-w | 9.30 | 9.50 | m | 9.33 | 9.47 | m |
| 9.98 | 8.85 | vw | 12.50 | 7.08 | w-m | 12.47 | 7.09 | w-m |
| 11.68 | 7.57 | vw | 15.27 | 5.80 | vw-w | 12.85 | 6.88 | vw |
| 12.62 | 7.00 | w | 15.58 | 5.68 | w | 14.62 | 6.05 | vw-w |
| 13.69 | 6.46 | vw-w | 17.70 | 5.01 | vw-w | 15.27 | 5.80 | w |
| 15.33 | 5.77 | vw-w | 18.72 | 4.74 | vw-m | 15.57 | 5.68 | w |
| 16.48 | 5.37 | vw-w | 19.28 | 4.60 | w | 16.60 | 5.34 | w |
| 17.01 | 5.20 | vw | 22.61** | 3.93 | w-m | 17.70 | 5.01 | vw-w |
| 17.70 | 5.01 | vw-w | 22.8-23.2* | 3.90-3.83 | vs | 18.71 | 4.74 | w-m |
| 19.20 | 4.62 | w-m | 23.43 | 3.79 | s | 19.30 | 4.59 | w |
| 21.59 | 4.11 | vw-w | 24.20 | 3.68 | m | 22.55 | 3.94 | m |
| 22.61** | 3.93 | w-m | 25.12 | 3.54 | m | 22.86** | 3.89 | m-s |
| 22.89 | 3.88 | vs | 26.34 | 3.38 | w-m | 23.03 | 3.86 | vs |
| 23.49 | 3.78 | m | 26.75 | 3.33 | w-m | 23.39 | 3.80 | s |

TABLE A3-continued

| I high TUN, low IMF | | | II med TUN, med IMF | | | III low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 23.93 | 3.72 | vw-w | 28.74-29.25* | 3.10-3.05 | w-m | 24.17 | 3.68 | m |
| 24.13 | 3.68 | m | 35.72 | 2.51 | vw-w | 25.01 | 3.56 | m |
| 24.64 | 3.61 | w | 45.29 | 2.00 | w | 26.19 | 3.40 | vw-w |
| 24.93 | 3.57 | w | 45.62-47.19* | 1.99-1.92 | vw-w | 26.68 | 3.34 | w-m |
| 25.31 | 3.52 | m | | | | 28.76 | 3.10 | w-m |
| 26.62 | 3.35 | w | | | | 35.72 | 2.51 | vw-w |
| 29.10 | 3.07 | w | | | | 45.08 | 2.01 | w |
| 35.72 | 2.51 | vw-w | | | | 45.62-47.19* | 1.99-1.92 | vw-w |
| 45.08 | 2.01 | w | | | | | | |
| 45.62-47.19* | 1.99-1.92 | vw-w | | | | | | |

*composite peak consisting of multiple overlapping reflections
**Typically a shoulder In Tables A2 and A3, the term "high" refers to about 60 to about 95 mass-% of the specified component, the term "med" refers to about 25 to about 70 mass-% of the specified component, and the term "low" refers to about 5 to about 40 mass-% of the specified component. Some peaks may be shoulders on more intense peaks, and some peaks may be a composite peak consisting of multiple overlapping reflections.

The UZM-39 material is thermally stable up to a temperature of at least about 600° C., or up to at least about 700° C., or up to at least about 800° C. The UZM-39 material may have a micropore volume as a percentage of total pore volume of greater than about 60%.

Characterization of the UZM-39 product by high-resolution scanning electron microscopy shows that the UZM-39 forms in lathes which assemble into rectangular rod particles, often with a starburst cluster arrangement.

UZM-39 is a coherently grown composite structure of TUN and IMF zeotypes. By coherently grown composite structure is meant that both structures are present in a major portion of the crystals in a given sample. This coherently grown composite structure is possible when the two zeotypic structures have nearly identical spacial arrangements of atoms along at least a planar projection of their crystal structure and possess similar pore topologies. Each vertex is a tetrahedral site (or T-site) and in the middle of each stick is a corner-shared oxygen atom. Along these projections, both the TUN and IMF zeotypes contain nearly identical projections of chains of 5-rings connected by 6-rings and 10-rings which form channels running perpendicular to the plane.

As both the TUN and IMF zeotypes are 3-dimensional 10-ring zeolites and have nearly identical projections in one plane, the two structures can thereby coherently grow off crystals of the other structure with interfaces at the compatible planes to form a coherently grown composite structure.

A coherently grown composite structure is not a physical mixture of the two molecular sieves. Electron diffraction, transmission electron microscopy and x-ray diffraction analysis are employed to show that a material is a coherently grown composite structure instead of a physical mixture. Usually the combination of electron diffraction and TEM imaging is most definitive in determining whether one has produced a coherently grown composite structure because it provides direct evidence of the existence of both structures within one crystal.

Since the coherently grown composite structure zeolites can have varying amounts of the two structure types, it is to be understood that the relative intensity and line width of some of the diffraction lines will vary depending on the amount of each structure present in the coherently grown composite structure. Although the degree of variation in the x-ray powder diffraction patterns is theoretically predictable for specific structures, the more likely mode of a coherently grown composite structure is random in nature and therefore difficult to predict without the use of large hypothetical models as bases for calculation.

Unlike a physical mixture of TNU-9 and IM-5, transmission electron microscopy (TEM) analysis using high resolution imaging and computed optical diffractograms shows that UZM-39 is comprised of a coherently grown composite structure of TUN and IMF zeotypes.

Additionally, UZM-39 zeolite can be characterized by Rietveld analysis of the XRD pattern. Rietveld analysis is a least-squares approach developed by Rietveld (*Journal of Applied Crystallography* 1969, 2: 65-71) to refine a theoretical line XRD profile until it matches the measured XRD pattern as closely as possible and is the preferred method of deriving structural information from samples such as UZM-39 which contain strongly overlapping reflections. It is often used to quantify the amounts of two different phases in a XRD diffractogram. The accuracy of the Rietveld method is determined by parameters such as crystallite size (peak broadening), peak shape function, lattice unit cell constants and background fits. Applicants have determined the error in the reported value may be ±5% under the conditions used. Applicants have also determined that the Rietveld model used was unable to quantify the amounts of minority composite structure phase component at values less than 10%. However, amounts of the minority component can be seen at levels greater than 5% visually by comparing against the model patterns. The Rietveld refinement results on various UZM-39 samples and shows that UZM-39 contains greater than 0 and less than 100 wt. % IMF zeotype and less than 100 wt. % and greater than 0 wt. % TUN zeotype. In another embodiment, UZM-39 contains greater than about 5 and less than about 95 wt. % IMF zeotype and less than about 95 wt. % and greater than about 5 wt. % TUN zeotype, and in yet another embodiment, UZM-39 contains greater than about 10 and less than about 90 wt. % IMF zeotype and less than about 90 wt. % and greater than about 10 wt. % TUN zeotype. A wide range of coherently grown composite structures are possible by modifying the synthesis conditions.

As synthesized, the UZM-39 material will contain some exchangeable or charge balancing cations in its pores. These exchangeable cations can be exchanged for other cations, or in the case of organic cations, they can be removed by heating under controlled conditions. It is also possible to remove some organic cations from the UZM-39 zeolite directly by ion exchange. The UZM-39 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination, ion-exchange and calcination and on an anhydrous basis, the modified microporous crystalline zeolite UZM-39 (UZM-39M) has a three-dimensional framework of at least $AlO_2$ and $SiO_2$ tetrahedral units and an empirical composition in the hydrogen form expressed by an empirical formula of $$M1_a^{N+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z'' is the mole ratio of O to (Al+E) and has a value determined by the equation:

$$z''=(a \cdot N+3+4 \cdot y')/2$$

In the hydrogen form, after calcination, ion-exchange and calcination to remove $NH_3$, UZM-39 displays the XRD pattern shown in Table B1-B3. Those peaks characteristic of UZM-39 are shown in Tables B1-B3 for various coherently grown composite structures. Additional peaks, particularly those of very weak intensity, may also be present. All peaks of medium or higher intensity present in the UZM-39 family of coherently grown composite structures are represented in at least Tables B3.

Table B1 contains selected d-spacings and relative intensities of the hydrogen form of UZM-39 X-ray diffraction pattern. The relative intensities are shown as a range covering UZM-39 materials with varying relative amounts of TUN and IMF zeotypes.

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections

The zeolite may be further characterized by the x-ray diffraction pattern having at least the d-spacings and intensities set forth in Table B2 where the d-spacings and intensities are provided at different relative concentrations of the components of the coherently grown composite structure.

TABLE B2

| A high TUN, low IMF | | | B med TUN, med IMF | | | C low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.12 | 12.40 | w-m | 7.11 | 12.42 | w-m | 7.16 | 12.25 | vw-w |
| 7.5-8.1* | 11.78-10.91 | m | 7.5-8.1* | 11.78-10.91 | m-s | 7.5-8.1* | 11.78-10.91 | m-s |
| 8.84 | 10.00 | m-s | 8.84 | 10.00 | m-s | 8.84 | 10.00 | m-s |
| 9.06 | 9.75 | m | 9.08 | 9.73 | m | 9.06** | 9.75 | w |
| 9.24** | 9.56 | vw-w | 9.24 | 9.56 | m | 9.24 | 9.56 | m |
| 12.53 | 7.06 | w | 12.48 | 7.09 | m | 12.46 | 7.10 | m |
| 22.89 | 3.88 | vs | 22.56** | 3.94 | w-m | 22.56 | 3.94 | w-m |
| 23.40 | 3.80 | m | 22.75-23.2* | 3.90-3.83 | vs | 23.06 | 3.85 | vs |
| 24.23 | 3.67 | w-m | 23.40 | 3.80 | s | 23.40 | 3.80 | s |
| 25.22 | 3.53 | m | 24.17 | 3.68 | m | 24.12 | 3.69 | m |
| 29.08 | 3.07 | w-m | 24.92-25.37* | 3.57-3.51 | m | 25.06 | 3.55 | m |
| 45.36 | 2.00 | w | 28.71-29.27* | 3.11-3.05 | w-m | 28.82 | 3.10 | w-m |
| | | | 45.34 | 2.00 | w | 45.32 | 2.00 | w |

*composite peak consisting of multiple overlapping reflections
**Typically a shoulder The zeolite may be yet further characterized by the x-ray diffraction pattern having at least the d-spacings and intensities set forth in Table B3 where the d-spacings and intensities are provided at different relative concentrations of the components of the coherently grown composite structure.

TABLE B3

| I high TUN, low IMF | | | II med TUN, med IMF | | | III low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.12 | 12.40 | w-m | 7.11 | 12.42 | w-m | 7.16 | 12.25 | vw-w |
| 7.5-8.1* | 11.78-10.91 | m | 7.5-8.1* | 11.78-10.91 | m-s | 7.5-8.1* | 11.78-10.91 | m-s |
| 8.84 | 10.00 | m-s | 8.84 | 10.00 | m-s | 8.84 | 10.00 | m-s |
| 9.06 | 9.75 | m | 9.08 | 9.73 | m | 9.06** | 9.75 | w |
| 9.24** | 9.56 | vw-w | 9.24 | 9.56 | m | 9.24 | 9.56 | m |
| 12.53 | 7.06 | w | 11.76 | 7.52 | vw-w | 11.76 | 7.52 | vw-w |
| 14.38 | 6.15 | w | 12.48 | 7.09 | m | 12.46 | 7.10 | m |
| 14.64 | 6.05 | vw | 14.38 | 6.15 | vw-w | 14.38 | 6.15 | vw |
| 15.26 | 5.80 | vw-w | 14.64 | 6.05 | vw-w | 14.64 | 6.05 | w |
| 15.52 | 5.70 | vw | 15.26 | 5.80 | w | 15.26 | 5.80 | w |
| 16.46 | 5.38 | vw | 15.52 | 5.70 | w-m | 15.52 | 5.70 | w-m |
| 17.72 | 5.00 | w | 16.50 | 5.37 | vw-w | 16.58 | 5.34 | w |
| 22.56** | 3.94 | vw-w | 17.72 | 5.00 | w-m | 17.72 | 5.00 | w-m |
| 22.89 | 3.88 | vs | 18.64 | 4.76 | vw-w | 18.64 | 4.76 | w |
| 23.06** | 3.85 | w-m | 22.56** | 3.94 | w-m | 22.56 | 3.94 | w-m |
| 23.40 | 3.80 | m | 22.75-23.2* | 3.90-3.83 | vs | 23.06 | 3.85 | vs |
| 23.82 | 3.73 | w-m | 23.40 | 3.80 | s | 23.40 | 3.80 | s |
| 24.23 | 3.67 | w-m | 24.17 | 3.68 | m | 24.12 | 3.69 | m |
| 24.70 | 3.60 | w-m | 24.70 | 3.60 | w-m | 25.06 | 3.55 | m |
| 25.22 | 3.53 | m | 24.92-25.37* | 3.57-3.51 | m | 26.16 | 3.40 | vw-w |
| 26.51 | 3.36 | w-m | 26.32 | 3.38 | w | 26.74 | 3.33 | w-m |
| 29.08 | 3.07 | w-m | 26.76 | 3.33 | w-m | 28.82 | 3.10 | w-m |
| 35.86 | 2.50 | vw-w | 28.71-29.27* | 3.11-3.05 | w-m | 30.12 | 2.96 | w |
| 45.36 | 2.00 | w | 30.13 | 2.96 | vw-w | 35.86 | 2.50 | vw-w |
| 45.66-47.37* | 1.98-1.91 | vw-w | 35.86 | 2.50 | vw-w | 45.32 | 2.00 | w |
| | | | 45.34 | 2.00 | w | 45.66-47.37* | 1.98-1.91 | vw-w |
| | | | 45.66-47.37* | 1.98-1.91 | vw-w | | | |

*composite peak consisting of multiple overlapping reflections
**Typically a shoulder In Tables B2 and B3, the term "high" refers to about 60 to about 95 mass-% of the specified component, the term "med" refers to about 25 to about 70 mass-% of the specified component, and the term "low" refers to about 5 to about 40 mass-% of the specified component. Some peaks may be shoulders on more intense peaks, and some peaks may be a composite peak consisting of multiple overlapping reflections.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

UZM-39 or UZM-39M may be enhanced in order to increase the pX/X ratio achieved during toluene disproportionation Enhancement is meant to indicate a step that increases the pX/X molar ratio significantly above the equilibrium value of 0.24 during toluene disproportionation. Three known examples are deposition of carbon, treatment with silica, and steaming following deposition of carbon and/or silica.

It has been surprisingly found that a catalyst comprising UZM-39 which has undergone an enhancement step until the pX/X molar ratio achieved during disproportionation conditions is greater than 0.6 had a unique combination of high pX/X molar ratio and high total xylene selectivity without production of excess benzene.

The catalyst may further comprise a refractory binder or matrix for the purpose of facilitating fabrication of the disproportionation catalyst, providing strength, reducing fabrication costs, or combinations thereof. The binder may be uniform in composition and relatively refractory to the conditions used in the process. Suitable binders may include inorganic oxides such as one or more of alumina, magnesia, zirconia, chromia, titania, boria, thoria, zinc oxide and silica. Alumina and/or silica are preferred binders. The amount of zeolite present in the bound catalyst can vary considerably but usually is present in an amount from about 30 to 90 mass percent and preferably from about 50 to 80 mass percent of the catalyst.

An exemplary enhancement step to deposit silica comprises exposing the zeolite to a silicon reagent, such as tetraethylorthosilicate (TEOS), followed by a calcination step. The exemplary enhancement by silica treatment incorporates silica onto the zeolite. The enhancement by deposition of silica may be effected by treatment of the zeolite, may be carried out on the zeolite prior to binding with a refractory oxide, or may be carried out on the bound catalyst.

In an aspect, UZM-39 may be extruded with a metal oxide binder prior to enhancement. Ion-exchanged zeolite powder may be extruded as cylinders or trilobes with refractory metal oxides comprising $SiO_2$, $TiO_2$, $ZrO_2$, $Al_2O_3$, or mixtures thereof. In an aspect, the refractory metal oxide may be $SiO_2$. Relative loadings of zeolite and refractory metal oxide may vary. Zeolite content in the catalyst extrudate may be greater than 50 wt %, or greater than 55 wt %, or greater than 60 wt %, or greater than 65 wt %, or less than 95 wt %, or less than 90 wt %, or less than 80 wt %. Extrudate size and shape may vary within known technical bounds, with cylinders and trilobes of approximately 1.6 mm preferred. Extrudate width may be from 0.75 mm to about 4 mm, or from about 1.0 mm to about 3 mm.

Dried extrudate may be calcined in air for from about 5 minutes to about 6 hours at temperatures in the range of about 350° C. to about 600° C. Times of about 15 minutes to about 4 hours, or about 30 minutes to about 3 hours may be acceptable. Temperatures of from about 400° C. to about 550° C., or from about 450° C. to about 550° C. may be acceptable. Optionally, extrudates may be ion-exchanged at 75° C. for 1 hour using a 10:1:1 weight ratio of water ammonium nitrate:extrudate. If ion-exchanged, the extrudate would be rinsed multiple times with deionized $H_2O$. If utilized, ion-exchange may be repeated if necessary. The final dried extrudate may then be calcined as described above.

Enhancement treatment by silica may proceed by placing the sample in a container, and adding an organic solvent. In an aspect, the amount of organic solvent to be added may be determined from Table 1. The container may be heated for 1 hour at reflux temperature of the organic solvent, during which time water may be removed from the system. The silicon reagent may then be added to the container. In an aspect, the silicon reagent includes, but is not limited to, a silicon alkoxide. Suitable silicon alkoxides include, but are not limited to, tetramethyl orthosilicate (TMOS), tetraethyl orthosilicate (TEOS), tetrapropyl orthosilicate (TPOS), tetraisopropyl orthosilicate (TiPOS), tetrabutyl orthosilicate (TBOS). The silicon reagent may be partially hydrolyzed alkoxides or siloxanes of silicon. A suitable source may be one of the Dynaslan® Silbond® family of products available from Evonik. The silicon reagent may be a chlorosilane. Concentration of the silicon reagent used may be in the range of 5 to 25 wt % on a basis of the sample weight.

Once the silicon reagent has been added, the contents of the container may be reacted at reflux from about 5 minutes to about 8 hours, or from about 30 minutes to about 4 hours. After reflux, solvent may be removed from the sample. Suitable solvent removal methods may involve decanting, distillation, or reduced pressure distillation. The sample may then be exposed to a heat treatment step of at least about 175° C. up to about 600° C. to form the enhanced catalyst. The enhancement treatment may be repeated as many times as needed to achieve the desired pX/X selectivity.

The enhancement by deposition of carbon may be effected at conditions relative to the subsequent disproportionation step comprising one or more of a higher temperature, lower pressure, higher space velocity, or higher hydrogen to hydrocarbon ratio. Such carbon deposition conditions may comprise a pressure of from about 100 kPa to 4 MPa absolute, and a liquid hourly space velocity of from about 0.2 to 10 $hr^{-1}$. The conditions may comprise one or more of an inlet temperature at least about 50° C. higher than the reaction temperature; a pressure at least about 100 kPa lower than the reaction pressure, or preferably no more than about half of the pressure utilized in the subsequent disproportionation step. Preferably, the molar ratio of free hydrogen to feedstock coke-forming hydrocarbons is no more than about half of that utilized in the subsequent disproportionation step. Lower pressure and/or a lower hydrogen/hydrocarbon ratio will lower the proportion of exothermic aromatic-saturation reactions, and thus restrict the temperature rise; the result should be a relatively flatter temperature profile. Thus, a typical temperature range would be from about 300° C. to about 700° C., and a typical hydrogen to coke-forming feed range would be about 0.01 to about 5 Enhancement by deposition of carbon may result in a catalyst carbon content of between about 5 and 40 mass-% carbon, and preferably between about 10 and 30 mass-% carbon. A coke-forming feed for deposition of carbon may comprise the feedstock to the disproportionation step as described below. In an aspect, toluene, or other specific hydrocarbons or mixtures known in the art preferably comprising aromatics may be used as the coke forming feed.

The UZM-39 may be enhanced one or more times with carbon and/or silica. The enhancement may incorporate carbon or silica into the catalyst comprising zeolite. Into means into or onto the surface of and is meant to indicate that the carbon or silica enhancement may deposit material onto the external surfaces of zeolite crystals, and/or on the exterior surfaces and/or within the pore structure of any refractory oxide present. Without wishing to be bound by theory, into does not describe depositing of material within the micropores of the zeolite. In an embodiment, enhancement may be carried out on the zeolite, may be carried out on the zeolite prior to binding with said refractory oxide, or may be carried out on the bound catalyst, comprising UZM-39 or UZM-39M. Individual enhancement steps may be repeated until a desired selectivity is achieved at disproportionation conditions. In an aspect, enhancement steps may be carried out until pX/X is greater than 0.6, or greater than 0.7, or greater than 0.8, or greater than 0.85, or greater than 0.9.

Following enhancement by deposition of carbon or deposition of silica, the enhanced UZM-39 may optionally undergo a steaming treatment. Steaming after enhancement may increase the pX/X achieved during disproportionation. However, steaming may also reduce the activity of the zeolite or catalyst. In an aspect, the steaming treatment conditions may utilize a temperature of from 100° C. to 750° C., or from about 200° C. to about 700° C., or from about 450° C. to about 650° C.; a partial pressure of water of about 0.1 to about 0.5, or about 0.15 to about 0.35; for a time of from about 10 minutes to about 26 hours, or from about 30 minutes to about 6 hours. In an aspect, high pX/X ratios during disproportionation may be achieved by enhancement step or steps, or by a combination of enhancement step or steps and steaming step or steps. Steaming and enhancement steps may be carried out in any order found to achieve high pX/X.

The enhanced UZM-39 zeolite of this invention may be utilized as a catalyst or catalyst support in the toluene disproportionation process.

The toluene disproportionation process comprises contacting a feed stream comprising toluene with a catalyst comprising a zeolite at disproportionation conditions to yield an effluent stream comprising benzene and xylenes. In a selective disproportionation process such as that of the instant invention, the catalyst may have been enhanced by one or more treatment steps in order to increase the molar ratio of para-xylene to xylene (pX/X) from the equilibrium level of about 0.24 to 0.60 or more by deposition of sufficient amounts of coke or silica. Although this enhancement increases the pX/X molar ratio, it has previously been accompanied by an increase in the molar ratio of benzene to xylene (Bz/X) to significantly greater than the theoretical value of 1. Using the best silica deposition technology to increase pX/X molar ratio to 0.90 or more, it has been common to see Bz/X molar ratio values up to 1.4 at disproportionation conditions which may comprise 30% toluene conversion, $H_2/HC=2$, WHSV=4 $hr^{-1}$, at a pressure of 2.8 MPa(g).

Ideally, the toluene disproportionation process operates at the highest toluene conversion possible while maximizing the xylene yield from the reaction. In an aspect, the toluene conversion may be greater than about 20 wt %, or greater than about 25 wt % or greater than about 28 wt % or greater than about 30 wt % or greater than 32 wt % or greater than about 35 wt % or less than about 50 wt %, or less than about 40 wt %, or less than about 35 wt %.

The feed for the disproportionation reaction may comprise toluene, optionally in combination with $C_9$ aromatics, and suitably is derived from one or a variety of sources. The feedstock may be produced synthetically, for example, from naphtha by catalytic reforming, or by pyrolysis followed by hydrotreating to yield an aromatics-rich product. The feedstock may be derived from such product with suitable purity by extraction of aromatic hydrocarbons from a mixture of aromatic and nonaromatic hydrocarbons and fractionation of the extract. For instance, aromatics may be recovered from a reformate. The feed may comprise at least about 80% toluene by mass, or greater than about 85% toluene, or greater than about 90% toluene, or greater than about 95% toluene, or even greater than about 98.5% toluene. The feed may comprise greater than about 90% aromatic compounds by mass, or greater than about 95% aromatic compounds, or greater than about 98% aromatic compounds, or greater than about 99% aromatic compounds, or even greater than about 99.5% aromatic compounds. In an aspect, the feedstock may contain no more than about 10% non-aromatic compounds by mass. In an aspect, the feed may contain no more than about 10% benzene by mass. In an aspect, the feed may contain no more than about 10% xylenes by mass. In an aspect, the feed may contain no more than 10% A9 aromatic compounds by mass. Desirably, non-aromatic compounds, benzene, xylenes, and A9 aromatic compounds are close to 0% by mass. In an aspect, all or mixtures of any of the conditions listed in this paragraph may apply to the characterization of the feed.

The disproportionation reaction conditions may include a temperature in the range of from about 200° C. to about 600° C., or from about 300° C. to about 450° C., or from 350° C. to about 425° C. The pressure may be in the range from about 1.0 MPa to about 7.0 MPa, or about 1.4 MPa(g) to about 4.5 MPa(g), or about 2.0 MPa(g) to about 3.5 MPa(g).

The disproportionation reaction can be effected over a wide range of space velocities, with higher space velocities effecting a higher ratio of para-xylene at the expense of conversion. The weight hourly space velocity (WHSV) may be in the range of about 0.5 to about 10 hr$^{-1}$, or about 1.0 to about 7 hr$^{-1}$, or about 1.0 to about 5 hr$^{-1}$. The ratio of hydrogen to hydrocarbon is calculated based on the molar ratio of free hydrogen compared against the feedstock hydrocarbon. Periodic increases in hydrogen to hydrocarbon above about 0.5, and preferably in the range of about 1 to about 5 may permit catalyst rejuvenation by hydrogenation of soft coke. The hydrogen to hydrocarbon ratio may be in the range of about 0.25 to about 10, or about 0.5 to about 5.

The molar ratio of para-xylene to xylene (pX/X) in the effluent is an important factor in the selective toluene disproportionation process. The equilibrium pX/X is about 0.24 at toluene disproportionation conditions, so a para-selective toluene disproportionation process produces an effluent comprising a pX/X of greater than about 0.25, or greater than about 0.30. The effluent from the toluene disproportionation process may have a pX/X molar ratio of greater than about 0.60, or greater than about 0.70, or greater than about 0.75, or greater than about 0.80, or greater than about 0.85, or greater than about 0.90, and may be less than about 0.98, or less than about 0.96, or less than about 0.94.

Ideally, the toluene disproportionation process operates at a benzene to xylene molar ratio (Bz/X) in the effluent of 1.00. A Bz/X of 1.00 indicates that for every mole of benzene produced, a mole of xylene is produced. Bz/X ratios closer to 1.00 are preferred, and in an aspect, the Bz/X molar ratio may be less than about 1.20, or less than about 1.16, or less than about 1.12, or less than about 1.08, or less than about 1.06, or less than about 1.05, or less than about 1.04, or less than about 1.03, or less than about 1.02, or less than about 1.01, and greater than about 1.00, or greater than about 0.99, or greater than about 0.98. For example, in some embodiments, the Bz/X ratio is in the range of about 0.98 to about 1.20 over a pX/X molar ratio in the range of about 0.25 to about 0.95. In some embodiments, the Bz/X ratio is in the range of about 0.98 to about 1.16 over a pX/X molar ratio of about 0.25 to about 0.95. In some embodiments, the Bz/X ratio is in the range of about 0.98 to about 1.12 over a pX/X molar ratio in the range of about 0.25 to about 0.95. In some embodiments, the Bz/X ratio is in the range of about 0.98 to about 1.08 over a pX/X molar ratio in the range of about 0.25 to about 0.95. In some embodiments, the Bz/X ratio is in the range of about 0.98 to about 1.06 over a pX/X molar ratio in the range of about 0.25 to about 0.90. In some embodiments, the Bz/X ratio is in the range of about 0.98 to about 1.05 over a pX/X molar ratio in the range of about 0.25 to about 0.85. In some embodiments, the Bz/X ratio is in the range of about 0.98 to about 1.02 over a pX/X molar ratio in the range of about 0.25 to about 0.85. In some embodiments, the Bz/X ratio is in the range of about 0.98 to about 1.01 over a pX/X molar ratio in the range of about 0.25 to about 0.80. In some embodiments, the Bz/X ratio is in the range of about 1.00 to about 1.20 over a pX/X molar ratio in the range of about 0.80 to about 0.95. In some embodiments, the Bz/X ratio is in the range of about 1.00 to about 1.16 over a pX/X molar ratio in the range of about 0.80 to about 0.95. In some embodiments, the Bz/X ratio is in the range of about 1.00 to about 1.12 over a pX/X molar ratio in the range of about 0.80 to about 0.95. In some embodiments, the Bz/X ratio is in the range of about 1.00 to about 1.08 over a pX/X molar ratio in the range of about 0.80 to about 0.95. In some embodiments, the Bz/X ratio is in the range of about 1.00 to about 1.06 over a pX/X molar ratio of about 0.80 to about 0.90.

When the feed contains benzene or xylenes, the amount of benzene or xylenes or para-xylene in the feed is subtracted from the amount in the product in order to determine the Bz/X ratio and pX/X ratio. In other words:

$$Bz/X \text{ molar ratio} = (Bz_{product} - Bz_{Feed})/(X_{product} - X_{Feed}).$$

Additionally, the para-xylene to total xylene molar ratio may be determined by pX/X molar ratio=$(pX_{product}$-p-$X_{Feed})/(X_{Product}-X_{Feed})$=PXX.

A relationship exists between the benzene to xylene molar ratio Bz/X and the para-xylene to xylene molar ratio pX/X, with increasing Bz/X as pX/X increases. Surprisingly, catalysts comprising UZM-39 suffer significantly less than previously known catalysts from this problem. Hence, when pX/X is in a range of about 0.60 to about 1.0, Bz/X may be in a range of about 1.00 to about 0.375*PXX+0.825, where PXX is the para-xylene to xylene molar ratio. Without being bound by theory, this equation allows one skilled in the art to calculate that at a pX/X of 0.60, the Bz/X may be in the range of about 1.00 to about 1.05. At a pX/X of 0.80, the Bz/X may be in the range of about 1.00 to about 1.13. At a pX/X of 0.90, the Bz/X may be in the range of about 1.00 to about 1.16.

Very high selectivity to xylenes at all pX/X ratios may be achieved utilizing enhanced catalysts made using UZM-39, even at pX/X molar ratios greater than about 0.8. The selectivity to xylene may be greater than 52% at a pX/X molar ratio in the range of about 0.3 to about 0.9 or more, or greater than 53% at a pX/X molar ratio in the range of about 0.3 to about 0.85 or more, or greater than 54% at a pX/X molar ratio in the range of about 0.3 to about 0.85 or more, or greater than 55% at a pX/X molar ratio in the range of about 0.3 to about 0.8 or more. In an aspect, all or mixtures of any of the conditions listed in this paragraph may apply at a pX/X molar ratio in the range of about 0.6 to about 0.95 or at a pX/X molar ratio in the range of about 0.8 to about 0.95.

Very low selectivity to light ends (e.g., $C_1$-$C_6$ hydrocarbons) may be achieved utilizing enhanced catalysts made using UZM-39 at all pX/X molar ratios, even at pX/X molar ratios greater than about 0.8. The selectivity to light ends may be less than about 3.5 wt % at a pX/X molar ratio in the range of about 0.3 to about 0.9 or more, or less than about 3 wt % at a pX/X molar ratio in the range of about 0.3 to about 0.9 or more, or less than about 2 wt % at a pX/X molar ratio in the range of about 0.3 to about 0.85 or more, or less than about 1.5 wt % at a pX/X molar ratio in the range of about 0.3 to about 0.8 or more, or even less than about 1 wt % at a pX/X molar ratio in the range of about 0.3 to about 0.8 or more. In an aspect, all or mixtures of any of the conditions listed in this paragraph may apply at a pX/X molar ratio in the range of about 0.6 to about 0.95 or at a pX/X molar ratio in the range of about 0.8 to about 0.95.

Enhanced catalysts of the instant invention may possess low ring loss. Ring loss may be calculated by subtracting the moles of single-ring aromatic compounds in the product from the number of moles of single-ring aromatics in the feed divided by the number of moles of single-ring aromatics in the feed multiplied by 100. Hence, Ring loss= $(Ar_{product}-Ar_{Feed})/(Ar_{Feed})*100$. Single-ring aromatics may comprise benzene, toluene, xylenes, 9 carbon aromatic molecules, 10 carbon aromatic molecules, etc. Single-ring aromatics do not comprise naphthalene. Without being bound by theory, selectivity to light ends and ring loss may be proportional due to cracking. That is, catalysts with high selectivity to light ends may also have high ring loss. Light ends indicate non-aromatic hydrocarbons possessing 1 to 6 carbon atoms. In an aspect, methane, ethane, propane, butanes, pentanes, hexanes, and cyclohexane may comprise light ends. In an aspect, the ring loss may be less than about 1.5%, or less than about 1.4%, or less than about 1.3%, or less than about 1.2%, or less than about 1.1%, or less than about 1.0%, or less than about 0.8%, or less than about 0.65%, or less than about 0.5%.

In an aspect, the industry desires retention of methyl groups during disproportionation. Benzene has zero moles of methyl groups per mole of benzene, toluene 1 mole methyl groups per mole toluene, xylenes 2, etc. Methyl to phenyl ratio in a stream may be calculated by dividing the number of moles of methyl groups in the stream by the number of moles of single-ring aromatics in the stream. In an aspect, the methyl to phenyl ratio of the product may be similar to the methyl to phenyl ratio of the feed. MPP is calculated by dividing the methyl to phenyl ratio of the product stream by that of the feedstream. MPP may be greater than about 0.96, or 0.97, or 0.98, or 0.99, and less than 1.0.

The enhanced UZM-39 zeolite can be used in a toluene disproportion process, such as the one illustrated in FIG. 1. The toluene disproportionation process may comprise multiple modules. In an aspect, a feed stream 100 comprising toluene is combined with second stream 304 to form a combined feed stream 102 which is passed to a reaction zone 200. Within the disproportionation process, the feed stream or combined feed stream may be first heated by indirect heat exchange against the effluent of the reaction zone and then further heated in a fired heater. The resulting vaporous stream may then be passed through a reaction zone which may comprise one or more individual reactors. The feed desirably contains less than 10% benzene by mass, less than 10% xylenes by mass, less than 10% A9 aromatic compounds by mass, and less than 10% non-aromatic compounds by mass. Benzene, xylenes, A9 aromatic compounds, and non-aromatic compounds may be less than 5% by mass in combined feed stream 102. Desirably, all of these are close to 0% by mass.

The reaction zone 200 may comprise one or more reactors. The one or more reactors may be fixed bed reactors, wherein a fixed bed or beds of catalyst comprising UZM-39 are located. The use of a single reaction vessel having a fixed cylindrical bed of catalyst is preferred, but other reaction configurations utilizing moving beds of catalyst or radial-flow reactors may be employed if desired. Reaction conditions in the reaction zone 200 may comprise disproportionation reaction conditions as described previously.

Passage of the combined stream 102 through the reaction zone effects the production of a vaporous effluent 204 comprising hydrogen, product hydrocarbons, and unconverted feed hydrocarbons. An effluent 204 from the reaction zone 200 is generated in which the effluent 204 has a higher concentration of pX than that present in combined feed stream 102. In an aspect, the PXX may be higher than 0.6 or higher than 0.7, or higher than 0.8, or higher than 0.85, or higher than 0.9. Effluent 204 may be passed into a separation zone 300 to separate unreacted toluene from products benzene and xylenes. This effluent may be normally cooled by indirect heat exchange against the stream entering the reaction zone and then further cooled through the use of air or cooling water. The temperature of the effluent stream may be lowered by heat exchange sufficiently to effect the condensation of substantially all of the feed and product hydrocarbons having six or more carbon atoms per molecule. The resultant mixed-phase stream may be passed into a vapor-liquid separator wherein the two phases are separated and from which the hydrogen-rich vapor is recycled in a first recycle stream to the reaction zone.

The separation zone 300 may comprise one or more distillation columns. The condensate from the separator may be passed into a stripping column in which substantially all $C_5$ and lighter hydrocarbons present in the effluent are concentrated into an overhead stream and removed from the process. An aromatics-rich stream which is referred to as the disproportionation effluent stream may be recovered as net stripper bottoms. In an aspect, a benzene column and a toluene column may be present. The disproportionation effluent stream may be fed to the benzene column and the toluene column in the separation zone. A first stream 302 comprising benzene may be separated and utilized for other reaction operations in an aromatic complex, or may be routed to a tank for sale. In an aspect, first stream 302 may be an overhead stream from a benzene column. A second stream 304 comprising toluene may be separated. In an aspect, all or part of the second stream 304 may be recycled to the reaction zone as part of the combined feed stream 102. In an aspect, second stream 304 comprises less than 10% benzene by mass, or less than 5% benzene by mass, or less than 3% benzene by mass, or less than 1% benzene by mass. In an aspect, second stream 304 is essentially free of benzene. By "essentially free" we mean less than 0.1 mass %. In an aspect, second stream 304 comprises less than 10% xylene by mass, or less than 5% xylene by mass, or less than 3% xylene by mass, or less than 1% xylene by mass. In an aspect, second stream 304 is essentially free of xylene. In an aspect, second stream 304 may be an overhead stream of the toluene column. In an aspect, a bottom stream from the benzene column may feed the toluene column. A third stream 306 comprising xylene may be separated.

Third stream 306 may be utilized as is, depending on the para-xylene purity desired, or it may be passed to a pX purification section 400. In an aspect, the separation zone, or pX purification section, may also comprise a catalytic alkylaromatic zone for ethylbenzene conversion and dealkylation. The purification section 400 may comprise one or more pX purification devices. Many pX purification devices are known, and these include, but are not limited to, crystallization processes and adsorptive separation processes like the Parex™ process available from UOP. In each case, a purified pX stream 404 comprising up to 100% pX may be formed. The purification section 400 may also produce a reject stream 402 comprising meta-xylene (mX) and ortho-xylene (oX). Reject stream 402 may also comprise ethylbenzene (EB). The reject stream may be purged from the process. Exemplary uses of the reject stream may be as a feed to a xylene isomerization process such as the Isomar™ process available from UOP. The xylene isomerization product may be recycled back to purification section 400.

By the term "about," we mean within 10% of the value, or within 5%, or within 1%.

One aspect of the invention is a toluene disproportionation process. In one embodiment, the process comprises contacting a feed comprising toluene with a catalyst comprising a microporous crystalline zeolite at disproportionation conditions to produce an effluent stream comprising para-xylene and benzene, wherein a molar ratio of benzene to xylene in the effluent stream is in a range of about 1.00 to about 1.14, wherein a molar ratio of para-xylene to xylene in the effluent stream is in a range of about 0.80 to about 1.0, and wherein a conversion of toluene is about 20% to about 40%.

In some embodiments, the molar ratio of benzene to xylene is in the range of about 1.00 to about 1.08.

In some embodiments, the microporous crystalline zeolite comprises a coherently grown composite of TUN and IMF zeotypes having a three-dimensional framework of at least $AlO_2$ and $SiO_2$ tetrahedral units and an empirical composition in the hydrogen form after calcination, ion-exchange and calcination and on an anhydrous basis expressed by an empirical formula of $$M1_a^{N+}Al_{(1-x)}E_xSi_{y'}O_{z''}$$

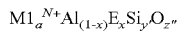

and where M1 is at least one exchangeable cation selected from the group consisting of alkali, alkaline earth metals, rare earth metals, zinc, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, "x" is the mole fraction of E and varies from 0 to about 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

wherein the zeolite is characterized in that it has the x-ray diffraction pattern having at least the d-spacings and intensities set forth in Table B1:

TABLE B1

| 2θ | d (Å) | I/Io % |
|---|---|---|
| 7.11-7.16 | 12.42-12.25 | vw-m |
| 7.5-8.1* | 11.78-10.91 | m-s |

TABLE B1-continued

| 2θ | d (Å) | I/Io % |
|---|---|---|
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections

In some embodiments, the catalyst has been enhanced with at least one enhancement treatment step.

In some embodiments, the at least one enhancement treatment step comprises at least one treatment to incorporate silica.

In some embodiments, the catalyst is steamed after the at least one enhancement treatment step.

In some embodiments, the molar ratio of benzene to xylene is in the range of about 1.00 to about 1.08 and wherein the range of the molar ratio of para-xylene to xylene is in the range of about 0.80 to about 0.95.

In some embodiments, the selectivity to xylenes is greater than 52% when the molar ratio of para-xylene to xylene is in the range of about 0.80 to about 0.90.

In some embodiments, the selectivity to light ends is less than about 3.5% is when the molar ratio of para-xylene to xylene is in the range of about 0.80 to about 0.90.

In some embodiments, the disproportionation conditions include one or more of: a temperature in a range of about 200° C. to about 600° C.; a pressure in a range of about 1.4 to about 4.5 MPa(g); a weight hourly space velocity in a range of about 0.1 to about 10 $hr^{-1}$; or a hydrogen to hydrocarbon ratio in a range of about 0.25:1 to about 10:1.

In some embodiments, ring loss is less than about 1.5%.

Another aspect of the invention is a toluene disproportionation process. In one embodiment, the process comprises contacting a feed comprising toluene with a catalyst comprising a microporous crystalline zeolite at disproportionation conditions to produce an effluent stream comprising para-xylene and benzene, wherein a molar ratio of benzene to xylene in the effluent stream is in a range of about 1.00 to about 1.20, wherein a molar ratio of para-xylene to xylene in the effluent stream is in a range of about 0.60 to about 1.0, the zeolite comprising a coherently grown composite of TUN and IMF zeotypes having a three-dimensional framework of at least $AlO_2$ and $SiO_2$ tetrahedral units and an empirical composition in the hydrogen form after calcination, ion-exchange and calcination and on an anhydrous basis expressed by an empirical formula of $$M1_a^{N+}Al_{(1-x)}E_xSi_{y'}O_{z''}$$

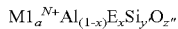

and where M1 is at least one exchangeable cation selected from the group consisting of alkali, alkaline earth metals, rare earth metals, zinc, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, "x" is the mole fraction of E and varies from 0 to about 1.0, y' is the mole ratio of Si to (Al+E) and varies from greater than about 9 to virtually pure silica and z" is the mole ratio of O to (Al+E) and has a value determined by the equation:

$$z''=(a\cdot N+3+4\cdot y')/2$$

wherein the zeolite is characterized in that it has the x-ray diffraction pattern having at least the d-spacings and intensities set forth in Table B1:

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections

In some embodiments, conversion of toluene is about 20% to about 40%.

In some embodiments, the zeolite has been enhanced with at least one enhancement selected from treatment for deposition of carbon, treatment for deposition of silica, or both.

In some embodiments, the catalyst is steamed after the at least one enhancement treatment step.

In some embodiments, the molar ratio of benzene to xylene is in the range of about 1.00 to about 1.08 and wherein the molar ratio of para-xylene to xylene is in the range of about 0.80 to about 0.95.

In some embodiments, the selectivity to xylenes is greater than 52% when the molar ratio of para-xylene to xylene is in the range of about 0.80 to about 0.90.

In some embodiments, the selectivity to light ends is less than about 3.5% is when the molar ratio of para-xylene to xylene is in the range of about 0.80 to about 0.90.

In some embodiments, the disproportionation conditions include one or more of: a temperature in a range of about 200° C. to about 600° C.; a pressure in a range of about 1.4 to about 4.5 MPa(g); a weight hourly space velocity in a range of about 0.1 to about 10 hr$^{-1}$; or a hydrogen to hydrocarbon ratio in a range of about 0.25 to about 10.

Another aspect of the invention is a toluene disproportionation process. In one embodiment, the process comprises contacting a feed comprising toluene with a catalyst comprising a microporous crystalline zeolite at disproportionation conditions to produce an effluent stream comprising para-xylene and benzene, wherein PXX is a molar ratio of para-xylene to xylene in the effluent stream, wherein BX is a molar ratio of benzene to xylene in the effluent stream, and wherein when PXX is in a range of about 0.60 to about 1.0, BX is in a range of about 1.00 to about 0.375*PXX+0.825.

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Examples

UZM-39 zeolite materials were prepared at approximately 28 SiO$_2$/Al$_2$O$_3$ ratio according to the procedures described in U.S. Pat. Nos. 8,642,823, 8,940,952, 8,946,497, and 8,846,998. Types A, B, and C UZM-39 are described above, and have high, medium, and low relative concentration of TUN in the material, respectively. MFI #1 is a MFI zeolite of approximately 38 SiO$_2$/Al$_2$O$_3$ ratio available from UOP. MFI #2 is a MFI zeolite of approximately 23 SiO$_2$/Al$_2$O$_3$ ratio available from Zeolyst.

Standard Catalyst Extrusion

Zeolites were typically extruded prior to enhancement. Ion-exchanged zeolite powder was extruded as ¹⁄₁₆" cylinders or trilobes with 35 wt % SiO$_2$, unless otherwise stated, and dried overnight. The dried extrudate was calcined in air for 2-4 hours at 550° C. In some cases, the extrudate was ion-exchanged at 75° C. for 1 hour using a 10:1:1 weight ratio of water ammonium nitrate:extrudate. If ion-exchanged, the sample was rinsed multiple times with deionized H$_2$O. Ion-exchange was repeated 3 times, and the final dried extrudate was calcined for 4 hours in air at 450-500° C.

General Enhancement Procedure:

The sample to be enhanced was placed in a glass round-bottom flask, and the appropriate amount of organic solvent from Table 1 was added. A Dean-Stark trap and condenser were attached to the round-bottom flask, filled with additional solvent, and insulated with tinfoil. The flask was heated with a heating mantle for 1 hour of reflux, after which the Dean-Stark trap was drained and removed from the flask. The tetraethylorthosilicate or other silicon reagent was added to the flask at 14 wt % on a basis of the sample weight unless otherwise specified. The condenser was reattached, and the contents of the flask were reacted at reflux for 2 hours. Solvent was then removed from the sample via decanting, distillation, or reduced pressure distillation. The sample then went through a heat treatment step of at least 175° C. to form the enhanced catalyst. The enhancement treatment was repeated as many times as needed to achieve the desired pX/X selectivity.

TABLE 1

Weight ratio of solvent to base extrudate for various solvents

| Solvent | Solvent to Base Wt. Ratio |
|---|---|
| Hexane | 1.76 |
| Toluene | 1.65 |
| Mesitylene (1,3,5-Trimethylbenzene) | 2.45 |
| n-octane | 2.53 |
| n-decane | 2.91 |
| Cyclohexane | 1.76 |

Example 1. Type C UZM-39 was used in a standard preparation with 5 treatment cycles.

Example 2. Type C UZM-39 was used in a standard preparation with 6 treatment cycles.

Example 3. Type C UZM-39 was used in a standard preparation with 7 treatment cycles.

Example 4. Type C UZM-39 was used in a standard preparation with 3 treatment cycles.

Example 5. Type C UZM-39 was used in a standard preparation with 5 treatment cycles.

Example 6. Type C UZM-39 was used in a standard preparation with 5 treatment cycles.

Example 7. Type C UZM-39 was used in a standard preparation with 7 treatment cycles.

Example 8. Type C UZM-39 was extruded as trilobes and used in a standard preparation with 3 treatment cycles.

Example 9. Type C UZM-39 was extruded as trilobes and used in a standard preparation with 5 treatment cycles.

Example 10. Type C UZM-39 was extruded as trilobes and used in a standard preparation with 6 treatment cycles.

Example 11. Type C UZM-39 was extruded as trilobes and used in a standard preparation with 7 treatment cycles.

Example 12. Type C UZM-39 was extruded as trilobes and used in a standard preparation with mesitylene as solvent and 3 treatment cycles where decanting was utilized as the solvent removal method.

Example 13. Type C UZM-39 was extruded as trilobes and used in a standard preparation with mesitylene as solvent and 4 treatment cycles where decanting was utilized as the solvent removal method.

Example 14. Type C UZM-39 was extruded as trilobes and used in a standard preparation with mesitylene as solvent and 5 treatment cycles where decanting was utilized as the solvent removal method.

Example 15. Type C UZM-39 was extruded as trilobes and used in a standard preparation with mesitylene as solvent and 6 treatment cycles where decanting was utilized as the solvent removal method.

Example 16. Type C UZM-39 was used in a standard preparation with mesitylene as solvent and 4 treatment cycles where decanting was utilized as the solvent removal method.

Example 17. Type C UZM-39 was used in a standard preparation with mesitylene as solvent and 5 treatment cycles where decanting was utilized as the solvent removal method.

Example 18. Type C UZM-39 was used in a preparation with mesitylene as solvent and 3 treatment cycles of 28% concentration of TEOS where decanting was utilized as the solvent removal method.

Example 19. Type B UZM-39 was used in a standard preparation with 3 treatment cycles.

Example 20. Type B UZM-39 was used in a standard preparation with 4 treatment cycles.

Example 21. Type B UZM-39 was used in a standard preparation with 5 treatment cycles.

Example 22. A composite of extruded UZM-39 materials of Type B average with an average of 4 cycles of enhancement by standard TEOS in toluene steps which had previously been run in toluene disproportionation and possessed 3% C content from previous contact with feed was made.

Example 23. Type B UZM-39 was used in a preparation with 1.9 solvent:catalyst ratio using toluene as solvent and TEOS as silicon source and rotary evaporation as solvent removal method. 3 enhancement steps were carried out.

Example 24. The material of Example 23 was treated once in a preparation with 10% TEOS in toluene at 1.9 solvent:catalyst ratio using rotary evaporation as solvent removal method.

Example 25. Type B UZM-39 was used in a standard preparation with 2 treatment cycles where rotary evaporation was the solvent removal method.

Example 26. Type B UZM-39 was used in a standard preparation with 3 treatment cycles where rotary evaporation was the solvent removal method.

Example 27. Type A UZM-39 was used in a standard preparation with mesitylene as solvent and 2 treatment cycles where decanting was utilized as the solvent removal method.

Example 28. The catalyst of Example 2 after running toluene disproportionation was calcined and then further enhanced by steaming at 650° C. for 20 minutes at a partial pressure of $H_2O$ of 0.2.

Example 29. The catalyst of Example 3 after running toluene disproportionation was calcined and then further enhanced by steaming at 650° C. for 20 minutes at a partial pressure of $H_2O$ of 0.2.

Comparative Examples 30-56. Examples 30-49 are made with MFI #1. Examples 50-56 are made with MFI #2.

Comparative Example 30. MFI #1 was used in a preparation with 3 treatment cycles using hexane as the solvent.

Comparative Example 31. MFI #1 was used in a standard preparation with 3 is treatment cycles.

Comparative Example 32. MFI #1 was used in a standard preparation with 3 treatment cycles.

Comparative Example 33. MFI #1 was used in a standard preparation with 4 treatment cycles.

Comparative Example 34. MFI #1 was used in a standard preparation with 3 treatment cycles.

Comparative Example 35. MFI #1 was used in a standard preparation with 4 treatment cycles.

Comparative Example 36. MFI #1 was used in a standard preparation with 3 treatment cycles.

Comparative Example 37. MFI #1 was used in a standard preparation with 4 treatment cycles.

Comparative Example 38. MFI #1 was used in a standard preparation with 3 treatment cycles where the solvent was removed by distillation.

Comparative Example 39. MFI #1 was extruded with $TiO_2$ at 70% zeolite content and treated with 4 standard treatment cycles.

Comparative Example 40. MFI #1 was used in a standard preparation with 3 treatment cycles.

Comparative Example 41. MFI #1 was used in a standard preparation with 2 treatment cycles.

Comparative Example 42. MFI #1 was used in a standard preparation prior to 3 treatment cycles using 20% TEOS in hexane.

Comparative Example 43. MFI #1 was used in a standard preparation with 3 treatment cycles using hexane as the solvent followed by a 190° C. heat step.

Comparative Example 44. MFI #1 was used in a standard preparation with 3 treatment cycles using hexane as solvent and distillation as solvent removal method.

Comparative Example 45. MFI #1 was used in a standard preparation with 2 treatment cycles using n-octane as solvent and decanting as solvent removal method.

Comparative Example 46. MFI #1 was used in a standard preparation with 3 treatment cycles using n-decane as solvent and decanting as solvent removal method.

Comparative Example 47. MFI #1 was used in a standard preparation with 3 treatment cycles using 10.2% TMOS in cyclohexane.

Comparative Example 48. MFI #1 was used in a standard preparation with 2 treatment cycles using 14% TBOS in toluene using rotary evaporation as the solvent removal method.

Comparative Example 49. MFI #1 was used in a standard preparation with 4 treatment cycles of Dynaslan Silbond, a TEOS derived product available from Evonik.

Comparative Example 50. MFI #2 was used in a standard preparation with 3 treatment cycles.

Comparative Example 51. MFI #2 was used in a standard preparation with 3 treatment cycles.

Comparative Example 52. MFI #2 was made into a spherical form at 70% zeolite content with $ZrO_2$ using the methods described in U.S. Pat. No. 4,629,717. The 70/30 MFI/$ZrO_2$ spheres were then enhanced with 3 treatment cycles.

Comparative Example 53. MFI #2 was used in a standard preparation with 1 treatment cycle using rotary evaporation as the solvent removal method.

Comparative Example 54. MFI #2 was used in a standard preparation with 2 treatment cycles using rotary evaporation as the solvent removal method.

Comparative Example 55. MFI #2 was used in a standard preparation with 3 treatment cycles using rotary evaporation as the solvent removal method.

Comparative Example 56. MFI #2 was used in a standard preparation where 1 cycle of 14% TEOS in mesitylene was used as solvent and decanting as solvent removal method.

Catalyst Testing Procedure:

The catalysts were tested in a disproportionation reaction using a feed of nominally 100 wt % toluene. The disproportionation reaction conditions were a WHSV of 4 hr$^{-1}$, a molar ratio of hydrogen to feed of 2, a pressure of 2.8 MPa(g) (400 psig), and temperatures from 350° C. to 460° C. The results achieved are shown in Table 2 and were compared at a target overall toluene conversion of 30 wt %.

Figure 2:
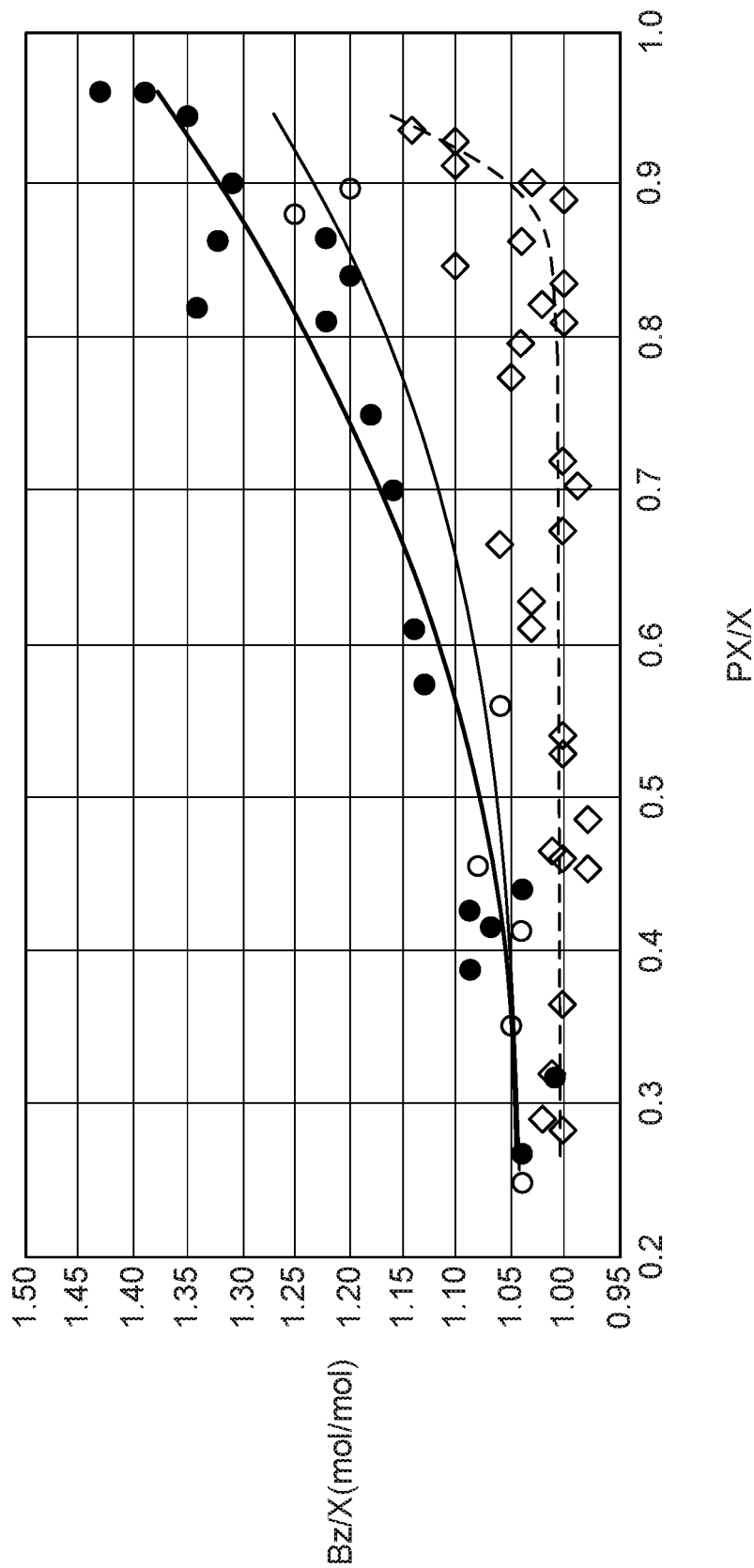
FIG. 2 is a graph showing the Bz/X molar ratio as a function of the pX/X molar ratio for various catalysts at 30% conversion.

FIG. 2 shows the results of Table 2 plotted as the benzene to xylene molar ratio in the product (Bz/X) versus the para-xylene molar ratio (pX/X) achieved. Catalysts made using MFI #1 are shown in black circles with dark black trendline, those made using MFI #2 in open circles with a gray trendline, and catalysts of the instant invention made with UZM-39 in open squares with a dashed trend-line. At all pX/X ratios, enhanced catalysts made using UZM-39 show very low Bz/X ratios, even at pX/X greater than 0.8. Catalysts made using MFI zeolite have Bz/X ratios of greater than 1.17 at pX/X greater than 0.85.

Figure 3:
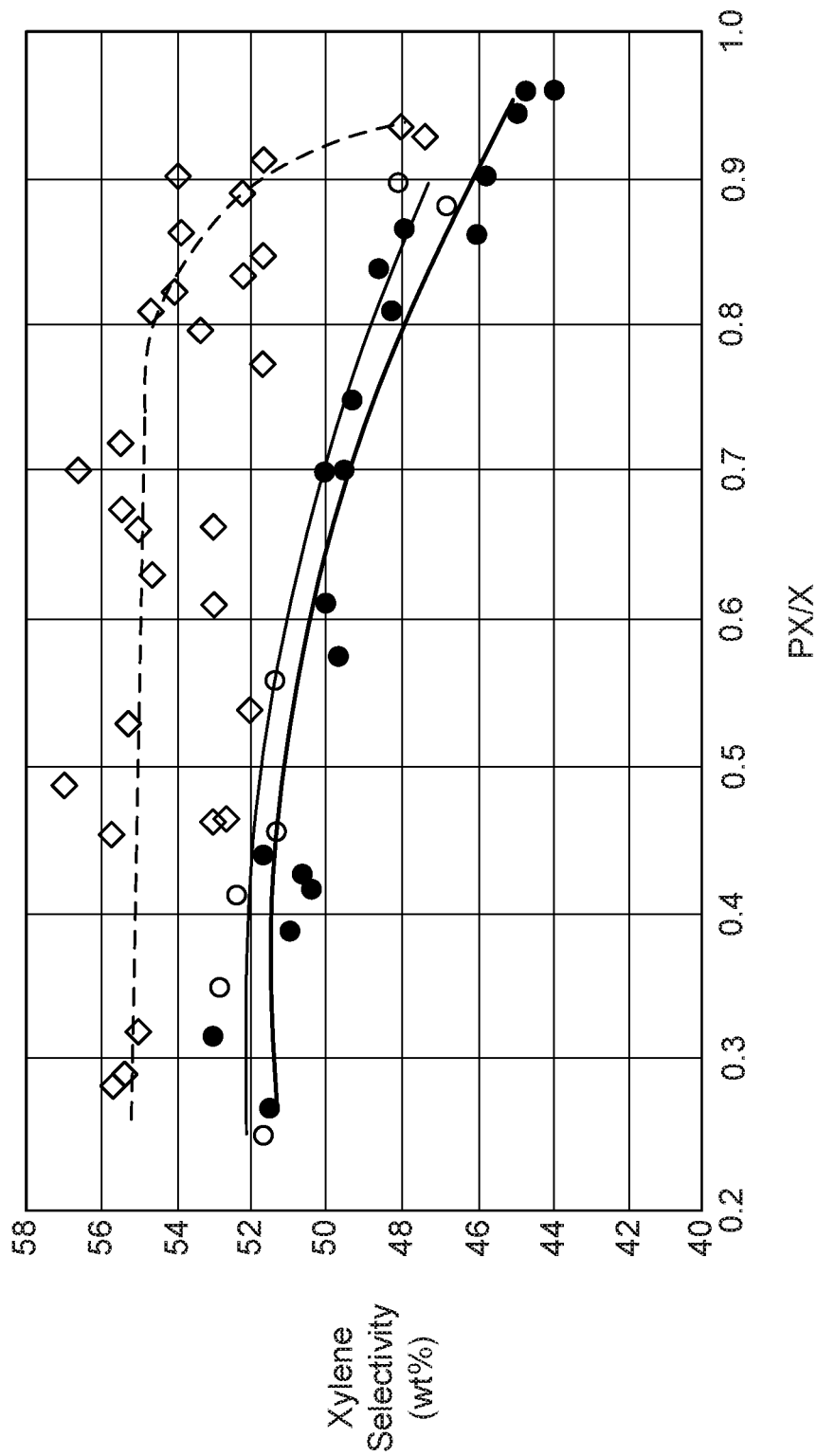
FIG. 3 is a graph showing the selectivity to xylene as a function of pX/X molar ratio for various catalysts at 30% conversion.

FIG. 3 shows the results of Table 2 plotted as the xylene selectivity in the product versus the para-xylene molar ratio (pX/X) achieved. Catalysts made using MFI #1 are shown in black circles with dark black trendline, those made using MFI #2 in open circles with a gray trendline, and catalysts of the instant invention made with UZM-39 in open squares with a dashed trend-line. At all pX/X ratios, enhanced catalysts made using UZM-39 show very high selectivity to xylenes, even at pX/X greater than 0.8 Catalysts made using UZM-39 may have selectivity to xylene greater than 52%, or greater than 53%, or greater than 54% at pX/X greater than 0.8, or greater than 0.85, or greater than 0.9.

Figure 4:
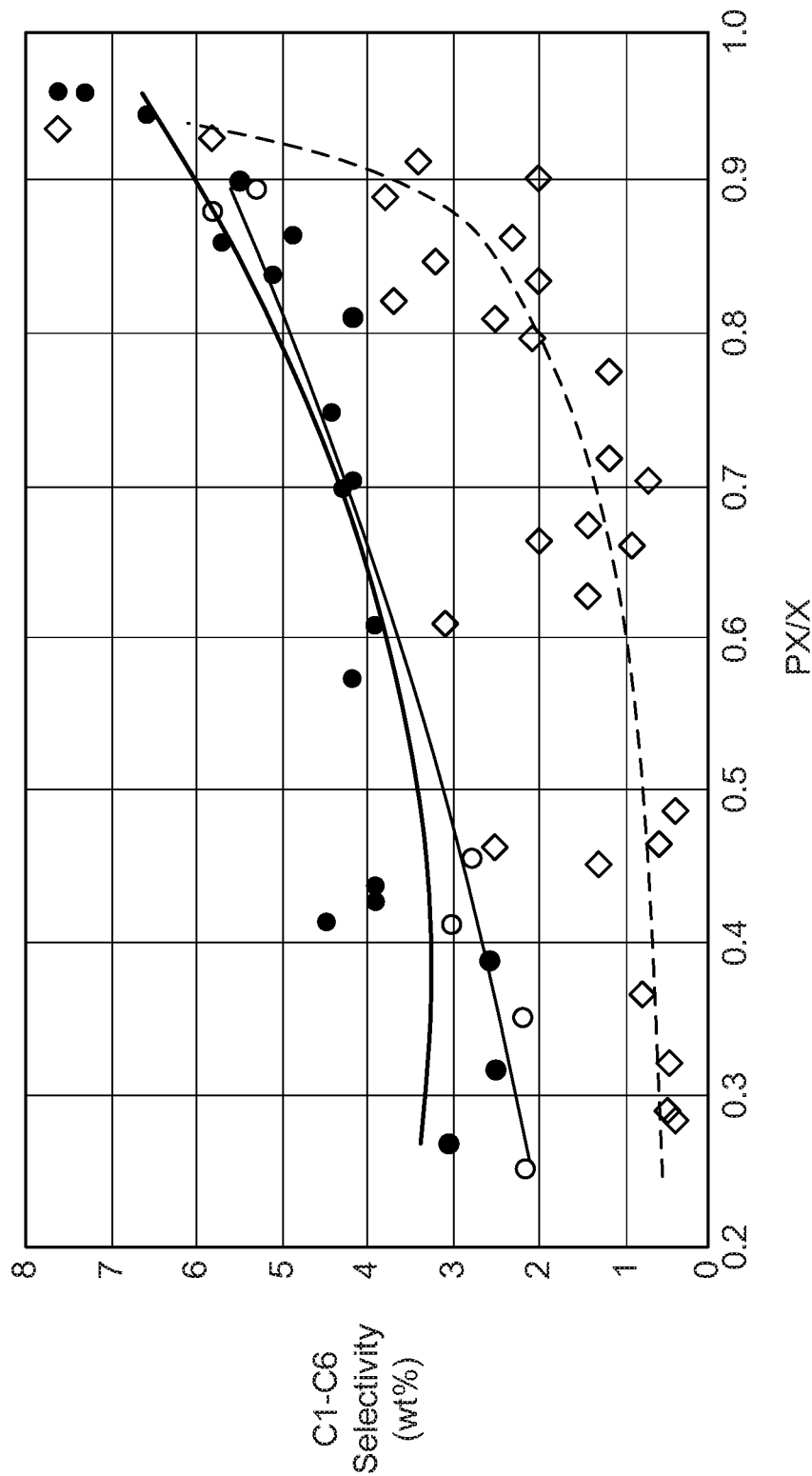
FIG. 4 is a graph showing the selectivity to light ends (C1-C6) as a function of pX/X molar ratio for various catalysts at 30% conversion.

FIG. 4 shows the results of Table 2 plotted as the selectivity to light ends (C1-C6 non-aromatic hydrocarbons) in the product versus the para-xylene molar ratio (pX/X) achieved. Catalysts made using MFI #1 are shown in black circles with dark black trendline, those made using MFI #2 in open circles with a gray trendline, and catalysts of the instant invention made with UZM-39 in open squares with a dashed trend-line. At all pX/X ratios, enhanced catalysts made using UZM-39 show very low selectivity to light ends, even at pX/X greater than about 0.8. Catalysts made using UZM-39 may have selectivity to light ends less than about 3.5 wt %, or less than about 3 wt %, or less than about 2 wt %, or less than about 1.5 wt %, or even less than about 1 wt % at pX/X of greater than about 0.8, or greater than about 0.85, or greater than about 0.9.

Figure 5:
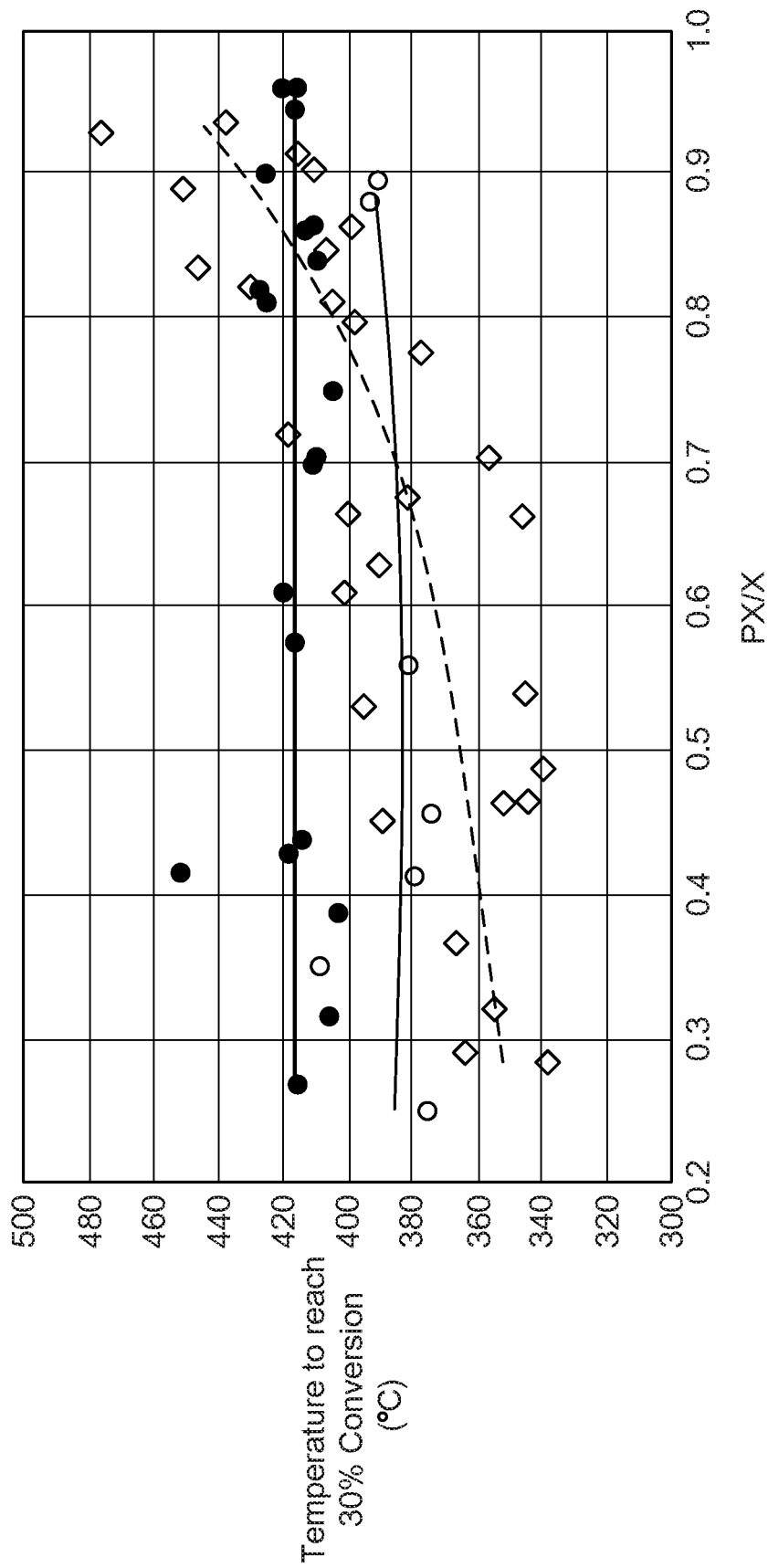
FIG. 5 is a graph showing the temperature required to achieve 30% conversion for various catalysts plotted against pX/X molar ratio achieved.

FIG. 5 shows the results of Table 2 plotted as the temperature required to reach 30% conversion of toluene versus the para-xylene molar ratio (pX/X) achieved. Catalysts made using MFI #1 are shown in black circles with dark black trendline, those made using MFI #2 in open circles with a gray trendline, and catalysts of the instant invention made with UZM-39 in open squares with a dashed trend-line.

The enhanced UZM-39 catalyst is completely unique. In addition to its surprisingly low Bz/X molar ratio, it shows higher total xylene yield, lower ring loss, lower light ends (e.g., $C_1$-$C_6$ hydrocarbons), and better methyl/phenyl retention than any of the other catalysts with similar pX/X molar ratio.

TABLE 2

| Example | UZM-39 or MFI type | pX/X at 30% Conversion | Bz/X at 30% Conversion | Temperature to reach 30% conversion | Xylene Selectivity at 30% conversion | C1-C6 Selectivity at 30% Conversion | solvent | Si source | [Si] | # Cycles | Solvent Removal Method |
|---|---|---|---|---|---|---|---|---|---|---|---|
| 1 | C | 0.53 | 1.00 | 395 | 55.3 | 0.9 | toluene | TEOS | 14 | 5 | |
| 2 | C | 0.72 | 1.00 | 418 | 55.5 | 1.2 | toluene | TEOS | 14 | 6 | |
| 3 | C | 0.89 | 1.00 | 450 | 52.2 | 3.8 | toluene | TEOS | 14 | 7 | |
| 4 | C | 0.29 | 1.02 | 364 | 55.3 | 0.5 | toluene | TEOS | 14 | 3 | |
| 5 | C | 0.64 | 1.00 | 645 | 52.0 | 0.8 | toluene | TEOS | 14 | 5 | |
| 6 | C | 0.68 | 1.00 | 381 | 55.4 | 1.4 | toluene | TEOS | 14 | 5 | |
| 7 | C | 0.90 | 1.03 | 410 | 54.0 | 2.0 | toluene | TEOS | 14 | 7 | |
| 8 | C | 0.28 | 1.00 | 338 | 55.6 | 0.4 | toluene | TEOS | 14 | 3 | |
| 9 | C | 0.49 | 0.98 | 339 | 56.9 | 0.4 | toluene | TEOS | 14 | 5 | |
| 10 | C | 0.70 | 0.99 | 356 | 56.6 | 0.7 | toluene | TEOS | 14 | 6 | |
| 11 | C | 0.86 | 1.04 | 399 | 53.9 | 2.3 | toluene | TEOS | 14 | 7 | |
| 12 | C | 0.32 | 1.01 | 355 | 55.0 | 0.5 | mesitylene | TEOS | 14 | 3 | decant |
| 13 | C | 0.47 | 1.01 | 344 | 52.7 | 0.6 | mesitylene | TEOS | 14 | 4 | decant |
| 14 | C | 0.66 | 0.94 | 346 | 55.0 | 0.9 | mesitylene | TEOS | 14 | 5 | decant |
| 15 | C | 0.85 | 1.10 | 407 | 51.7 | 3.2 | mesitylene | TEOS | 14 | 6 | decant |
| 16 | C | 0.46 | 1.00 | 352 | 53.0 | 2.5 | mesitylene | TEOS | 14 | 4 | decant |
| 17 | C | 0.61 | 1.03 | 401 | 53.0 | 3.1 | mesitylene | TEOS | 14 | 5 | decant |
| 18 | C | 0.78 | 1.05 | 377 | 51.7 | 1.2 | mesitylene | TEOS | 28 | 3 | decant |
| 19 | B | 0.45 | 0.98 | 389 | 55.7 | 1.3 | toluene | TEOS | 14 | 3 | |

TABLE 2-continued

| Example | UZM-39 or MFI type | pX/X at 30% Conversion | Bz/X at 30% Conversion | Temperature to reach 30% conversion | Xylene Selectivity at 30% conversion | C1-C6 Selectivity at 30% Conversion | solvent | Si source | [Si] | # Cycles | Solvent Removal Method |
|---|---|---|---|---|---|---|---|---|---|---|---|
| 20 | B | 0.81 | 1.00 | 405 | 54.6 | 2.5 | toluene | TEOS | 14 | 4 | |
| 21 | B | 0.94 | 1.14 | 438 | 48.0 | 7.6 | toluene | TEOS | 14 | 5 | |
| 22 | B | 0.82 | 1.02 | 430 | 54.0 | 3.7 | toluene | TEOS | 14 | 4 | |
| 23 | B | 0.63 | 1.03 | 390 | 54.7 | 1.4 | toluene | TEOS | 14 | 3 | |
| 24 | B | 0.91 | 1.10 | 415 | 51.7 | 3.4 | toluene | TEOS | 10 | 3.5 | |
| 25 | B | 0.37 | 1.00 | 367 | 60.0 | 0.8 | toluene | TEOS | 14 | 2 | |
| 26 | B | 0.80 | 1.04 | 398 | 53.3 | 2.1 | toluene | TEOS | 14 | 3 | |
| 27 | A | 0.67 | 1.06 | 400 | 53.0 | 2.0 | mesitylene | TEOS | 14 | 2 | |
| 28 | C | 0.84 | 1.00 | 446 | 52.2 | 2.0 | N/A | N/A | | 1 | |
| 29 | C | 0.93 | 1.10 | 476 | 47.4 | 5.8 | N/A | N/A | | 1 | |
| 30 | 1 | 0.61 | 1.14 | 421 | 50.0 | 3.9 | hexane | TEOS | 14 | 3 | |
| 31 | 1 | 0.70 | 1.16 | 410 | 50.0 | 4.3 | toluene | TEOS | 14 | 3 | |
| 32 | 1 | 0.84 | 1.20 | 409 | 48.7 | 5.1 | toluene | TEOS | 14 | 3 | |
| 33 | 1 | 0.96 | 1.39 | 420 | 44.7 | 7.6 | toluene | TEOS | 14 | 4 | |
| 34 | 1 | 0.75 | 1.18 | 405 | 49.3 | 4.4 | toluene | TEOS | 14 | 3 | |
| 35 | 1 | 0.96 | 1.43 | 416 | 44.0 | 7.3 | toluene | TEOS | 14 | 4 | |
| 36 | 1 | 0.70 | 1.16 | 409 | 49.5 | 4.2 | toluene | TEOS | 14 | 3 | distill |
| 37 | 1 | 0.94 | 1.35 | 416 | 45.0 | 6.6 | toluene | TEOS | 14 | 4 | distill |
| 38 | 1 | 0.57 | 1.13 | 416 | 49.7 | 4.2 | toluene | TEOS | 14 | 3 | |
| 39 | 1 | 0.44 | 1.04 | 414 | 51.7 | 3.9 | toluene | TEOS | 14 | 4 | |
| 40 | 1 | 0.86 | 1.22 | 410 | 47.9 | 4.9 | toluene | TEOS | 14 | 3 | |
| 41 | 1 | 0.32 | 1.01 | 406 | 53.0 | 2.5 | toluene | TEOS | 14 | 2 | |
| 42 | 1 | 0.81 | 1.22 | 425 | 48.3 | 4.2 | hexane | TEOS | 20 | 3 | |
| 43 | 1 | 0.90 | 1.31 | 425 | 45.7 | 5.5 | hexane | TEOS | 14 | 3 | |
| 44 | 1 | 0.42 | 1.07 | 451 | 50.3 | 4.5 | hexane | TEOS | 14 | 3 | distill |
| 45 | 1 | 0.27 | 1.04 | 415 | 51.5 | 3.0 | n-octane | TEOS | 14 | 2 | decant |
| 46 | 1 | 0.39 | 1.09 | 403 | 51.0 | 2.6 | n-decane | TEOS | 14 | 3 | decant |
| 47 | 1 | 0.86 | 1.32 | 413 | 46.0 | 5.7 | cyclohexane | TEOS | 10 | 3 | |
| 48 | 1 | 0.43 | 1.09 | 418 | 50.7 | 3.9 | toluene | TBOS | 14 | 2 | rotovap |
| 49 | 1 | 0.82 | 1.34 | 427 | | | | Silbond | | 4 | |
| 50 | 2 | 0.56 | 1.06 | 381 | 51.3 | | toluene | TEOS | 14 | 3 | |
| 51 | 2 | 0.90 | 1.20 | 391 | 48.1 | 5.3 | toluene | TEOS | 14 | 3 | |
| 52 | 2 | 0.35 | 1.05 | 408 | 52.8 | 2.2 | toluene | TEOS | 14 | 3 | |
| 53 | 2 | 0.25 | 1.04 | 375 | 51.7 | 2.2 | toluene | TEOS | 14 | 1 | rotovap |
| 54 | 2 | 0.41 | 1.04 | 379 | 52.4 | 3.0 | toluene | TEOS | 14 | 2 | rotovap |
| 55 | 2 | 0.88 | 1.25 | 393 | 46.8 | 5.8 | toluene | TEOS | 14 | 3 | rotovap |
| 56 | 2 | 0.46 | 1.08 | 374 | 51.3 | 2.8 | mesitylene | TEOS | 14 | 1 | decant |

SPECIFIC EMBODIMENTS

While the following is described in conjunction with specific embodiments, it will be understood that this description is intended to illustrate and not limit the scope of the preceding description and the appended claims.

A first embodiment of the invention is a process comprising contacting a feed comprising toluene with a catalyst comprising a microporous crystalline zeolite at disproportionation conditions to produce an effluent stream comprising para-xylene and benzene, wherein a molar ratio of benzene to xylene in the effluent stream is in a range of about 1.00 to about 1.14, wherein a molar ratio of para-xylene to xylene in the effluent stream is in a range of about 0.80 to about 1.0, and wherein a conversion of toluene is about 20% to about 40%. An embodiment of the invention is one, any or all of prior embodiments in this paragraph up through the first embodiment in this paragraph wherein the molar ratio of benzene to xylene is in the range of about 1.00 to about 1.08. An embodiment of the invention is one, any or all of prior embodiments in this paragraph up through the first embodiment in this paragraph wherein the microporous crystalline zeolite comprises a coherently grown composite of TUN and IMF zeotypes having a three-dimensional framework of at least $AlO_2$ and $SiO_2$ tetrahedral units and an empirical composition in the hydrogen form after calcination, ion-exchange and calcination and on an anhydrous basis expressed by an empirical formula of $$M1_a^{N+}Al_{(1-x)}E_xSi_{y'}O_{z''}$$

and where M1 is at least one exchangeable cation selected from the group consisting of alkali, alkaline earth metals, rare earth metals, zinc, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, "x" is the mole fraction of E and varies from 0 to about 1.0, y' is the mole ratio of Si to (Al+E) and varies from greater than about 9 to virtually pure silica and z" is the mole ratio of 0 to (Al+E) and has a value determined by the equation $$z''=(a \cdot N+3+4 \cdot y')/2$$

wherein the zeolite is characterized in that it has the x-ray diffraction pattern having at least the d-spacings and intensities set forth in Table B1:

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |

TABLE B1-continued

| 2θ | d (Å) | I/Io % |
|---|---|---|
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections

An embodiment of the invention is one, any or all of prior embodiments in this paragraph up through the first embodiment in this paragraph wherein the catalyst has been enhanced with at least one enhancement treatment step. An embodiment of the invention is one, any or all of prior embodiments in this paragraph up through the first embodiment in this paragraph wherein the at least one enhancement treatment step comprises at least one treatment to incorporate silica. An embodiment of the invention is one, any or all of prior is embodiments in this paragraph up through the first embodiment in this paragraph wherein the catalyst is steamed after the at least one enhancement treatment step. An embodiment of the invention is one, any or all of prior embodiments in this paragraph up through the first embodiment in this paragraph wherein the molar ratio of benzene to xylene is in the range of about 1.00 to about 1.08 and wherein the range of the molar ratio of para-xylene to xylene is in the range of about 0.80 to about 0.95. An embodiment of the invention is one, any or all of prior embodiments in this paragraph up through the first embodiment in this paragraph wherein a selectivity to xylenes is greater than 52% when the molar ratio of para-xylene to xylene is in the range of about 0.80 to about 0.90. An embodiment of the invention is one, any or all of prior embodiments in this paragraph up through the first embodiment in this paragraph wherein a selectivity to light ends is less than about 3.5% when the molar ratio of para-xylene to xylene is in the range of about 0.80 to about 0.90. An embodiment of the invention is one, any or all of prior embodiments in this paragraph up through the first embodiment in this paragraph wherein the disproportionation conditions include one or more of a temperature in a range of about 200° C. to about 600° C.; a pressure in a range of about 1.4 to about 4.5 MPa(g); a weight hourly space velocity in a range of about 0.1 to about 10 $hr^{-1}$; or a hydrogen to hydrocarbon ratio in a range of about 0.251 to about 101. An embodiment of the invention is one, any or all of prior embodiments in this paragraph up through the first embodiment in this paragraph wherein ring loss is less than about 1.5%.

A second embodiment of the invention is a process comprising contacting a feed comprising toluene with a catalyst comprising a microporous crystalline zeolite at disproportionation conditions to produce an effluent stream comprising para-xylene and benzene, wherein a molar ratio of benzene to xylene in the effluent stream is in a range of about 1.00 to about 1.20, wherein a molar ratio of para-xylene to xylene in the effluent stream is in a range of about 0.60 to about 1.0, the zeolite comprising a coherently grown composite of TUN and IMF zeotypes having a three-dimensional framework of at least $AlO_2$ and $SiO_2$ tetrahedral units and an empirical composition in the hydrogen form after calcination, ion-exchange and calcination and on an anhydrous basis expressed by an empirical formula of

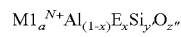

and where M1 is at least one exchangeable cation selected from the group consisting of alkali, alkaline earth metals, rare earth metals, zinc, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, "x" is the mole fraction of E and varies from 0 to about 1.0, y' is the mole ratio of Si to (Al+E) and varies from greater than about 9 to virtually pure silica and z" is the mole ratio of O to (Al+E) and has a value determined by the equation $$z''=(a \cdot N+3+4 \cdot y')/2$$

wherein the zeolite is characterized in that it has the x-ray diffraction pattern having at least the d-spacings and intensities set forth in Table B1:

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections

An embodiment of the invention is one, any or all of prior embodiments in this paragraph up through the second embodiment in this paragraph wherein conversion of toluene is about 20% to about 40%. An embodiment of the invention is one, any or all of prior embodiments in this paragraph up through the second embodiment in this paragraph wherein the zeolite has been enhanced with at least one enhancement selected from treatment for deposition of carbon, treatment for deposition of silica, or both. An embodiment of the invention is one, any or all of prior embodiments in this paragraph up through the second embodiment in this paragraph wherein the catalyst is steamed after the at least one enhancement treatment step. An embodiment of the invention is one, any or all of prior embodiments in this paragraph up through the second embodiment in this paragraph wherein the molar ratio of benzene to xylene is in the range of about 1.00 to about 1.08 and wherein the molar ratio of para-xylene to xylene is in the range of about 0.80 to about 0.95. An embodiment of the invention is one, any or all of prior embodiments in this paragraph up through the second embodiment in this paragraph wherein a selectivity to xylenes is greater than 52% when the molar ratio of para-xylene to xylene is in the range of about 0.80 to about 0.90. An embodiment of the invention is one, any or all of prior embodiments in this paragraph up through the second embodiment in this paragraph wherein a selectivity to light ends is less than about 3.5% when the molar ratio of para-xylene to xylene is in the range of about 0.80 to about 0.90. An embodiment of the invention is one, any or all of prior embodiments in this paragraph up through the second embodiment in this paragraph wherein the disproportionation conditions include one or more of a temperature in a range of about 200° C. to about 600° C.; a pressure in a range of about 1.4 to about 4.5 MPa(g); a weight hourly space velocity in a range of about 0.1 to about 10 hr$^{-1}$; or a hydrogen to hydrocarbon ratio in a range of about 0.25 to about 10.

A third embodiment of the invention is a process comprising contacting a feed comprising toluene with a catalyst comprising a microporous crystalline zeolite at disproportionation conditions to produce an effluent stream comprising para-xylene and benzene, wherein PXX is a molar ratio of para-xylene to xylene in the effluent stream, wherein BX is a molar ratio of benzene to xylene in the effluent stream, and wherein when PXX is in a range of about 0.60 to about 1.0, BX is in a range of about 1.00 to about 0.375*PXX+ 0.825.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A toluene disproportionation process comprising contacting a feed comprising toluene with a catalyst comprising a microporous crystalline zeolite at disproportionation conditions to produce an effluent stream comprising para-xylene and benzene, wherein a molar ratio of benzene to xylene in the effluent stream is in a range of about 1.00 to about 1.14, wherein a molar ratio of para-xylene to xylene in the effluent stream is in a range of about 0.80 to about 1.0, wherein a conversion of toluene is about 20% to about 40%; and
   wherein the zeolite has been enhanced with at least one enhancement selected from treatment for deposition of carbon, treatment for deposition of silica, or both.

2. The process of claim 1 wherein the molar ratio of benzene to xylene is in the range of about 1.00 to about 1.08.

3. The process of claim 1 wherein the microporous crystalline zeolite comprises a coherently grown composite of TUN and IMF zeotypes having a three-dimensional framework of at least AlO$_2$ and SiO$_2$ tetrahedral units and an empirical composition in the hydrogen form after calcination, ion-exchange and calcination and on an anhydrous basis expressed by an empirical formula of

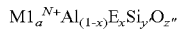

and where M1 is at least one exchangeable cation selected from the group consisting of alkali, alkaline earth metals, rare earth metals, zinc, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, "x" is the mole fraction of E and varies from 0 to about 1.0, y' is the mole ratio of Si to (Al+E) and is greater than about 9 and z" is the mole ratio of O to (Al+E) and has a value determined by the equation:

$$z''=(a \cdot N+3+4 \cdot y')/2$$

wherein the zeolite is characterized in that it has the x-ray diffraction pattern having at least the d-spacings and intensities set forth in Table B1:

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections.

4. The process of claim 1 wherein the at least one enhancement treatment step comprises at least one treatment to incorporate silica.

5. The process of claim 1 wherein the catalyst is steamed after the at least one enhancement treatment step.

6. The process of claim 1 wherein the molar ratio of benzene to xylene is in the range of about 1.00 to about 1.08 and wherein the range of the molar ratio of para-xylene to xylene is in the range of about 0.80 to about 0.95.

7. The process of claim 1 wherein a selectivity to xylenes is greater than 52% when the molar ratio of para-xylene to xylene is in the range of about 0.80 to about 0.90.

8. The process of claim 1 wherein a selectivity to light ends is less than about 3.5% when the molar ratio of para-xylene to xylene is in the range of about 0.80 to about 0.90.

9. The process of claim 1 wherein the disproportionation conditions include one or more of: a temperature in a range of about 200° C. to about 600° C.; a pressure in a range of about 1.4 to about 4.5 MPa(g); a weight hourly space velocity in a range of about 0.1 to about 10 hr$^{-1}$; or a hydrogen to hydrocarbon ratio in a range of about 0.25:1 to about 10:1.

10. The process of claim 1 wherein ring loss is less than about 1.5%.

11. A toluene disproportionation process comprising contacting a feed comprising toluene with a catalyst comprising a microporous crystalline zeolite at disproportionation conditions to produce an effluent stream comprising para-xylene and benzene, wherein a molar ratio of benzene to xylene in the effluent stream is in a range of about 1.00 to about 1.20, wherein a molar ratio of para-xylene to xylene in the effluent stream is in a range of about 0.60 to about 1.0, the zeolite comprising a coherently grown composite of TUN and IMF zeotypes having a three-dimensional framework of at least AlO$_2$ and SiO$_2$ tetrahedral units and an empirical composition in the hydrogen form after calcination, ion-exchange and calcination and on an anhydrous basis expressed by an empirical formula of

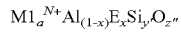

and where M1 is at least one exchangeable cation selected from the group consisting of alkali, alkaline earth metals, rare earth metals, zinc, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, "x" is the mole fraction of E and varies from 0 to about 1.0, y' is the mole ratio of Si to (Al+E) and is greater than about 9 and z" is the mole ratio of O to (Al+E) and has a value determined by the equation:

$$z''=(a \cdot N+3+4 \cdot y')/2$$

wherein the zeolite is characterized in that it has the x-ray diffraction pattern having at least the d-spacings and intensities set forth in Table B1:

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections and wherein the zeolite has been enhanced with at least one enhancement selected from treatment for deposition of carbon, treatment for deposition of silica, or both.

12. The process of claim 11 wherein conversion of toluene is about 20% to about 40%.

13. The process of claim 12 wherein the catalyst is steamed after the at least one enhancement treatment step.

14. The process of claim 11 wherein the molar ratio of benzene to xylene is in the range of about 1.00 to about 1.08 and wherein the molar ratio of para-xylene to xylene is in the range of about 0.80 to about 0.95.

15. The process of claim 11 wherein a selectivity to xylenes is greater than 52% when the molar ratio of para-xylene to xylene is in the range of about 0.80 to about 0.90.

16. The process of claim 11 wherein a selectivity to light ends is less than about 3.5% when the molar ratio of para-xylene to xylene is in the range of about 0.80 to about 0.90.

17. The process of claim 11 wherein the disproportionation conditions include one or more of: a temperature in a range of about 200° C. to about 600° C.; a pressure in a range of about 1.4 to about 4.5 MPa(g); a weight hourly space velocity in a range of about 0.1 to about 10 $hr^{-1}$; or a hydrogen to hydrocarbon ratio in a range of about 0.25 to about 10.

18. A toluene disproportionation process comprising contacting a feed comprising toluene with a catalyst comprising a microporous crystalline zeolite at disproportionation conditions to produce an effluent stream comprising para-xylene and benzene, wherein PXX is a molar ratio of para-xylene to xylene in the effluent stream, wherein BX is a molar ratio of benzene to xylene in the effluent stream, wherein PXX is in a range of about 0.60 to about 1.0, BX is in a range of about 1.00 to about 0.375*PXX+0.825; and wherein the zeolite has been enhanced with at least one enhancement selected from treatment for deposition of carbon, treatment for deposition of silica, or both.

* * * * *